United States Patent [19]
Guglielmi et al.

[11] Patent Number: 5,122,136
[45] Date of Patent: Jun. 16, 1992

[54] ENDOVASCULAR ELECTROLYTICALLY DETACHABLE GUIDEWIRE TIP FOR THE ELECTROFORMATION OF THROMBUS IN ARTERIES, VEINS, ANEURYSMS, VASCULAR MALFORMATIONS AND ARTERIOVENOUS FISTULAS

[75] Inventors: Guido Guglielmi, Los Angeles; Ivan Sepetka, Redwood City, both of Calif.

[73] Assignee: The Regents of the University of California, Oakland, Calif.

[21] Appl. No.: 492,717

[22] Filed: Mar. 13, 1990

[51] Int. Cl.⁵ .............................................. A61B 17/38
[52] U.S. Cl. ...................................... 606/32; 606/41; 128/772; 128/784
[58] Field of Search ....................... 606/32, 41, 49, 28; 128/772, 784, 786

[56] References Cited

U.S. PATENT DOCUMENTS

| | | | |
|---|---|---|---|
| 4,522,205 | 6/1985 | Taylor et al. | 606/49 |
| 4,735,201 | 4/1988 | O'Reilly | 606/28 |
| 4,748,986 | 6/1988 | Morrison | 128/772 |

FOREIGN PATENT DOCUMENTS 8801851  3/1988  World Int. Prop. O. ............ 606/49

Primary Examiner—Lee S. Cohen
Attorney, Agent, or Firm—Daniel L. Dawes

[57] ABSTRACT

An artery, vein, aneurysm, vascular malformation or arterial fistula is occluded through endovascular electrothrombosis by the endovascular insertion of a platinum guidewire tip into the vascular cavity followed by application of a positive current. The guidewire tip is then separated from the guidewire by electrolytic separation of the tip from the guidewire. A portion of the guidewire connected between the tip and the body of the guidewire is comprised of stainless steel and exposed to the bloodstream so that upon continued application of a positive current to the exposed portion, the exposed portion is corroded away at least at one location and the tip is separated from the body of the guidewire. The guidewire and the microcatheter are thereafter removed leaving the guidewire tip embedded in the thrombus formed within the vascular cavity.

23 Claims, 4 Drawing Sheets

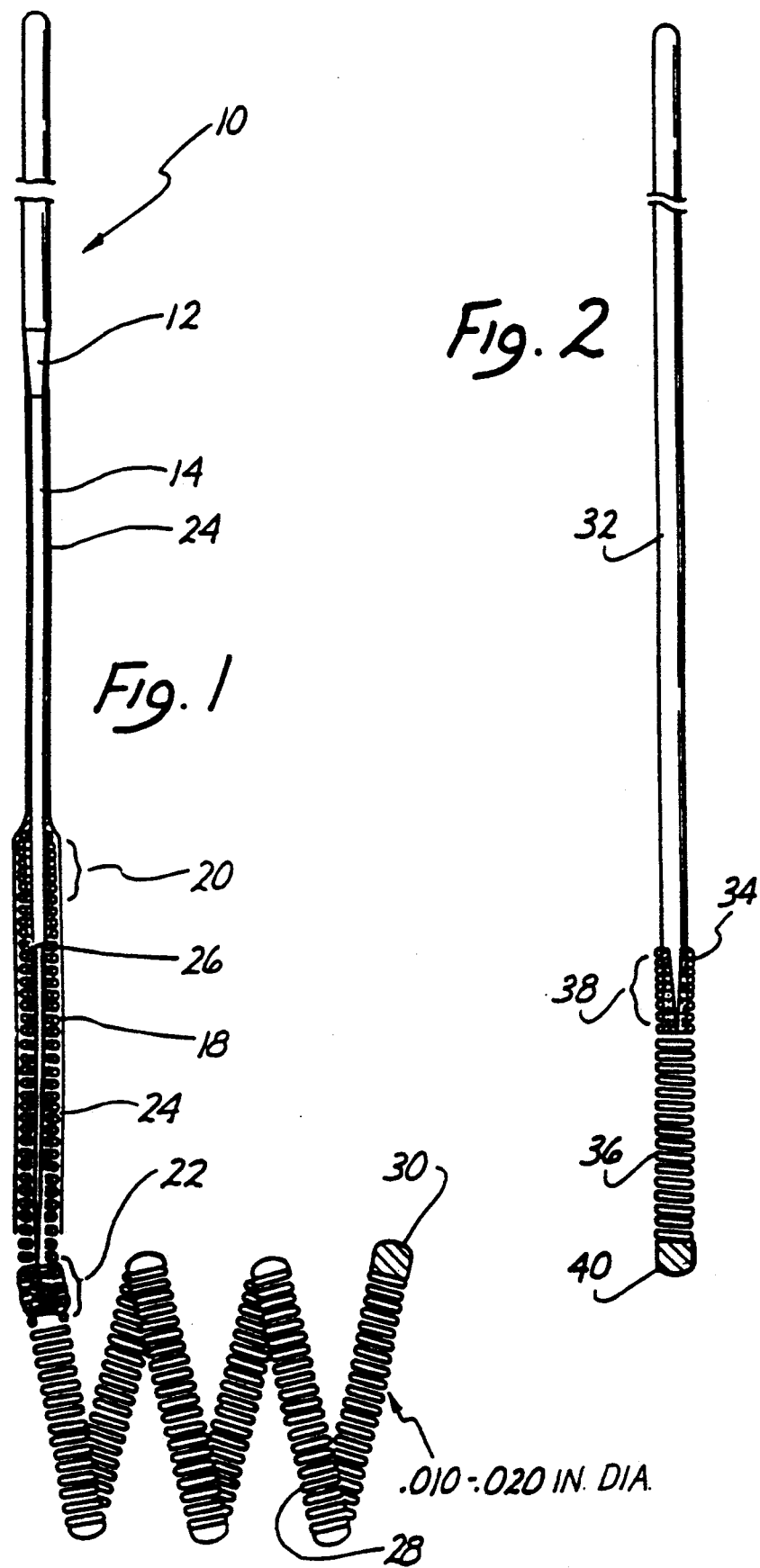

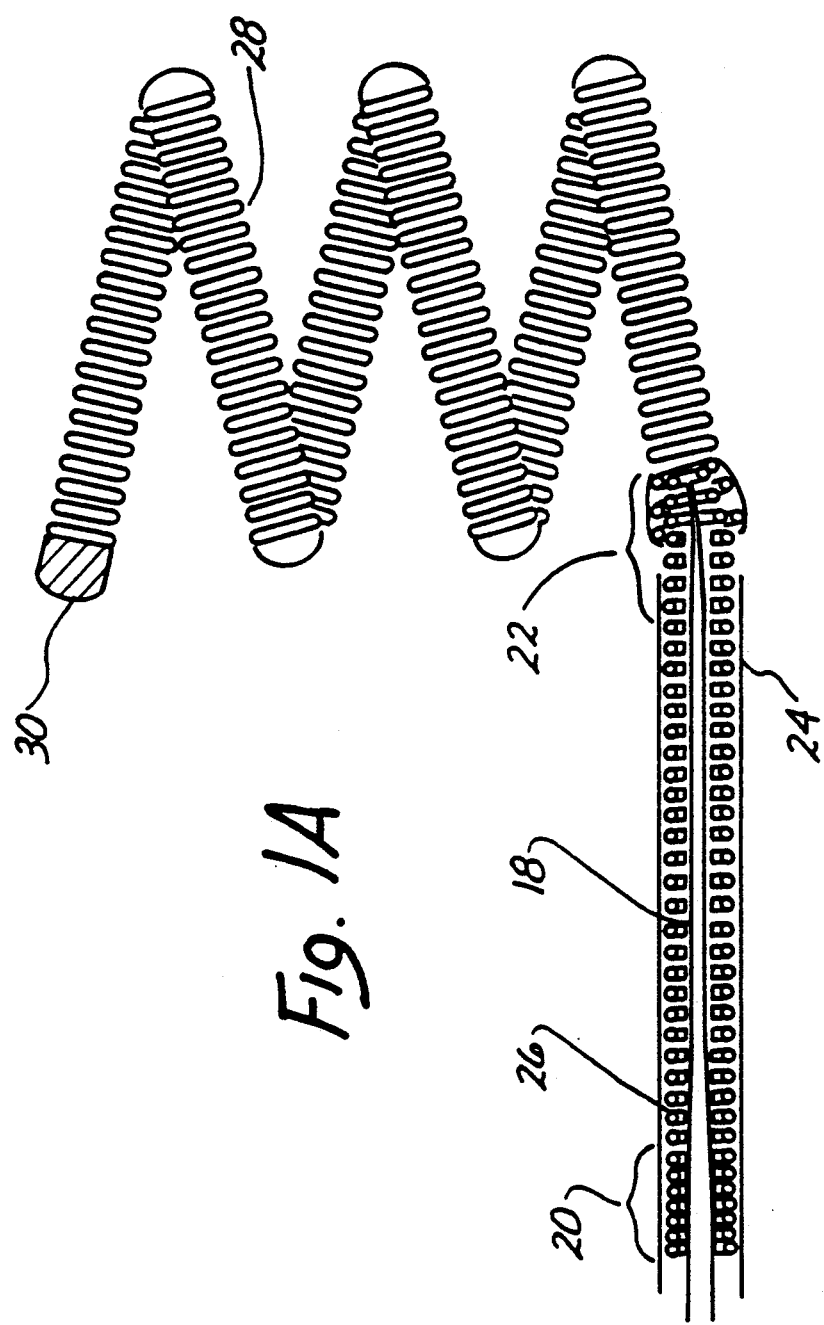
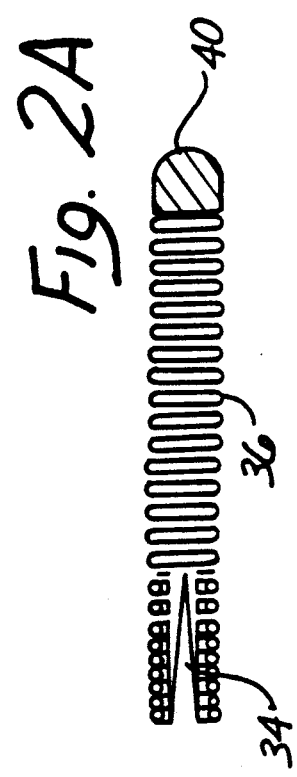

ENDOVASCULAR ELECTROLYTICALLY DETACHABLE GUIDEWIRE TIP FOR THE ELECTROFORMATION OF THROMBUS IN ARTERIES, VEINS, ANEURYSMS, VASCULAR MALFORMATIONS AND ARTERIOVENOUS FISTULAS

BACKGROUND OF THE INVENTION

1. Field of the Invention

The invention relates to a method and apparatus for endovascular electrothrombic formation of thrombi in arteries, veins, aneurysms, vascular malformations and arteriovenous fistulas.

2. Description of the Prior Art

Approximately 25,000 intracranial aneurysms rupture every year in North America. The primary purpose of treatment for ruptured intracranial aneurysm is to prevent rebleeding. At the present time, three general methods of treatment exist, namely an extravascular, endovascular and extra-endovascular approach.

The extravascular approach is comprised of surgery or microsurgery of the aneurysm or treatment site for the purpose of preserving the parent artery. This treatment is common with intracranial berry aneurysms. The methodology comprises the step of clipping the neck of the aneurysm, performing a sutureligation of the neck, or wrapping the entire aneurysm. Each of these surgical procedures is performed by intrusive invasion into the body and performed from outside the aneurysm or target site. General anesthesia, craniotomy, brain retraction and arachnoid dissection around the neck of the aneurysm and placement of a clip are typically required in these surgical procedures. Surgical treatment of vascular intracranial aneurysm can expect a mortality rate of 4–8% with a morbidity rate of 18–20%. Because of the mortality and morbidity rate expected, the surgical procedure is often delayed while waiting for the best surgical time with the result that an additional percentage of patients will die from the underlying disease or defect prior to surgery. For this reason the prior art has sought alternative means of treatment.

In the endovascular approach, the interior of the aneurysm is entered through the use of a microcatheter. Recently developed microcatheters, such as those shown by Engleson, "Catheter Guidewire", U.S. Pat. No. 4,884,579 and as described in Engleson, "Catheter for Guidewire Tracking", U.S. Pat. No. 4,739,768 (1988), allow navigation into the cerebral arteries and entry into a cranial aneurysm.

In such procedures a balloon is typically attached to the end of the microcatheter and it is possible to introduce the balloon into the aneurysm, inflate it, and detach it, leaving it to occlude the sac and neck with preservation of the parent artery. While endovascular balloon embolization of berry aneurysms is an attractive method in situations where an extravascular surgical approach is difficult, inflation of a balloon into the aneurysm carries some risk of aneurysm rupture due to possible over-distention of portions of the sac and due to the traction produced while detaching the balloon.

While remedial procedures exist for treating a ruptured aneurysm during classical extravascular surgery, no satisfactory methodology exists if the aneurysm breaks during an endovascular balloon embolization.

Furthermore, an ideal embolizing agent should adapt itself to the irregular shape of the internal walls of the aneurysm. On the contrary, in a balloon embolization the aneurysmal wall must conform to the shape of the balloon. This may not lead to a satisfactory result and further increases the risk of rupture.

Still further, balloon embolization is not always possible. If the diameter of the deflated balloon is too great to enter the intracerebral arteries, especially in the cases where there is a vasospasm, complications with ruptured intracranial aneurysms may occur. The procedure then must be deferred until the spasm is resolved and this then incurs a risk of rebleeding.

In the extra-intravascular approach, an aneurysm is surgically exposed or stereotaxically reached with a probe. The wall of the aneurysm is then perforated from the outside and various techniques are used to occlude the interior in order to prevent it from rebleeding. These prior art techniques include electrothrombosis, isobutyl-cyanoacrylate embolization, hog-hair embolization and ferromagnetic thrombosis.

In the use of electrothrombosis for extra-intravascular treatment the tip of a positively charged electrode is inserted surgically into the interior of the aneurysm. An application of the positive charge attracts white blood cells, red blood cells, platelets and fibrinogen which are typically negatively charged at the normal pH of the blood. The thrombic mass is then formed in the aneurysm about the tip. Thereafter, the tip is removed. See Mullan, "*Experiences with Surgical Thrombosis of Intracranial Berry Aneurysms and Carotid Cavernous Fistulas*", J. Neurosurg., Vol. 41, December 1974; Hosobuchi, "*Electrothrombosis Carotid-Cavernous Fistula*", J. Neurosurg., Vol. 42, January 1975; Araki et al., "*Electrically Induced Thrombosis for the Treatment of Intracranial Aneurysms and Angiomas*", Excerpta Medica International Congress Series, Amsterdam 1965, Vol. 110, 651–654; Sawyer et al., "*Bio-Electric Phenomena as an Etiological Factor in Intravascular Thrombosis*", Am. J. Physiol., Vol. 175, 103–107 (1953); J. Piton et al., "*Selective Vascular Thrombosis Induced by a Direct Electrical Current; Animal Experiments*", J. Neuroradiology, Vol. 5, pages 139–152 (1978). However, each of these techniques involves some type of intrusive procedure to approach the aneurysm from the exterior of the body.

The prior art has also devised the use of a liquid adhesive, isobutylcyanoacrylate (IBCA) which polymerizes rapidly on contact with blood to form a firm mass. The liquid adhesive is injected into the aneurysm by puncturing the sac with a small needle. In order to avoid spillage into the parent artery during IBCA injection, blood flow through the parent artery must be momentarily reduced or interrupted. Alternatively, an inflated balloon may be placed in the artery at the level of the neck of the aneurysm for injection. In addition to the risks caused by temporary blockage of the parent artery, the risks of seepage of such a polymerizing adhesive into the parent artery exists, if it is not completely blocked with consequent occlusion of the artery.

Still further, the prior art has utilized an air gun to inject hog hair through the aneurysm wall to induce internal thrombosis. The success of this procedure involves exposing the aneurysm sufficiently to allow air gun injection and has not been convincingly shown as successful for thrombic formations.

Ferromagnetic thrombosis in the prior art in extra-intravascular treatments comprises the stereotactic placement of a magnetic probe against the sac of the aneurysm followed by injection into the aneurysm by an injecting needle of iron microspheres. Aggregation of the microspheres through the extravascular magnet is followed by interneuysmatic thrombus. This treatment has not been entirely successful because of the risk of fragmentation of the metallic thrombus when the extravascular magnet is removed. Suspension of the iron powder in methyl methymethacrylate has been used to prevent fragmentation. The treatment has not been favored, because of the need to puncture the aneurysm, the risk of occlusion of the parent artery, the use of unusual and expensive equipment, the need for a craniectomy and general anesthesia, and the necessity to penetrate cerebral tissue to reach the aneurysm.

Endovascular coagulation of blood is also well known in the art and a device using laser optically generated heat is shown by O'Reilly, "*Optical Fiber with Attachable Metallic Tip for Intravascular Laser Coagulation of Arteries, Veins, Aneurysms, Vascular Malformation and Arteriovenous Fistulas*", U.S. Pat. No. 4,735,201 (1988). See also, O'Reilly et al., "*Laser Induced Thermal Occlusion of Berry Aneurysms: Initial Experimental Results*", Radiology, Vol. 171, No. 2, pages 471–74 (1989). O'Reilly places a tip into an aneurysm by means of an endovascular microcatheter. The tip is adhesively bonded to a optic fiber disposed through the microcatheter. Optical energy is transmitted along the optic fiber from a remote laser at the proximal end of the microcatheter. The optical energy heats the tip to cauterize the tissue surrounding the neck of the aneurysm or other vascular opening to be occluded. The catheter is provided with a balloon located on or adjacent to its distal end to cut off blood flow to the site to be cauterized and occluded. Normally, the blood flow would carry away the heat at the catheter tip, thereby preventing cauterization. The heat in the tip also serves to melt the adhesive used to secure the tip to the distal end of the optical fiber. If all goes well, the tip can be separated from the optical fiber and left in place in the neck of the aneurysm, provided that the cauterization is complete at the same time as the hot melt adhesive melts.

A thrombus is not formed from the heated tip. Instead, blood tissue surrounding the tip is coagulated. Coagulation is a denaturation of protein to form a connective-like tissue similar to that which occurs when the albumen of an egg is heated and coagulates from a clear running liquid to an opaque white solid. The tissue characteristics and composition of the coagulated tissue is therefore substantially distinct from the thrombosis which is formed by the thrombotic aggregation of white and red blood cells, platelets and fibrinogen. The coagulative tissue is substantially softer than a thrombic mass and can therefore more easily be dislodged.

O'Reilly's device depends at least in part upon the successful cauterization timed to occur no later than the detachment of the heat tip from the optic fiber. The heated tip must also be proportionally sized to the neck of the aneurysm in order to effectively coagulate the tissue surrounding it to form a blockage at the neck. It is believed that the tissue in the interior of the aneurysm remains substantially uncoagulated. In addition, the hot melt adhesive attaching the tip to the optic fiber melts and is dispersed into the adjacent blood tissue where it resolidifies to form free particles within the intracranial blood stream with much the same disadvantages which result from fragmentation of a ferromagnetic electrothrombosis.

Therefore, what is needed is an apparatus and methodology which avoids each of the shortcomings and limitations of the prior art discussed above.

BRIEF SUMMARY OF THE INVENTION

A method for forming a thrombus within a vascular cavity comprising the steps of endovascularly disposing a guidewire near an endovascular opening into the vascular cavity. A distal tip of the guidewire is disposed into the vascular cavity. An electrical signal is applied to the distal tip within the vascular cavity to form a thrombus within the vascular cavity about the distal tip. The distal tip is detached from the guidewire to leave the distal tip within the vascular cavity and the thrombus electrically formed within the vascular cavity.

As a result, electrical formation of a thrombus is completely endovascularly formed.

The step of disposing the distal tip in the vascular cavity further comprises the step of substantially occupying the vascular cavity with the distal tip.

In one embodiment the step of substantially occupying the vascular cavity comprises the step of filling the vascular cavity with a long and pliable length of the distal tip.

The step of detaching the distal tip from the guidewire comprises the step of electrolytically detaching the distal tip from the guidewire.

The step of electrolytically detaching the distal tip from the guidewire comprises the step of electrolytically disintegrating at least one portion of a connecting segment extending between the guidewire and the distal tip.

The step of electrolytically disintegrating the connecting segment comprises the step of electrolytically corroding away at least a portion of a coil segment.

The step of electrolytically corroding the coil segment comprises the step of electrolytically disintegrating a stainless steel coil segment.

The step of applying an electrical signal to the distal tip to form the thrombus comprises the step of applying a positive direct current for a first predetermined time period. The tip can be detached in at least three different ways. First, the same current for forming the thrombosis may also simultaneously be used to detach the tip. Second, the current, which forms the thrombosis or initiates the continuing formation of the thrombosis during a following period of no current, is followed by a current of the same or different magnitude during a second time period to effect detachment. Third, the thrombosis is formed during a time period during which the disintegratable portion of the tip is arranged and configured not to be exposed to the blood. The guidewire is then repositioned so the disintegratable portion is exposed to electrolytic disintegration in the blood by application of the same or different level of current for an additional time period to effect detachment.

The invention is also a guidewire for use in electrothrombosis and used in combination with a microcatheter comprising a core wire. The core wire has a distal portion susceptible to electrolytic disintegration in blood. A tip portion is coupled to the distal portion of the core wire. The tip portion is provided for endovascular insertion within a vascular cavity.

As a result, endovascular electrothrombosis is achieved.

The distal portion is an exposed stainless steel segment.

The stainless steel segment comprises a coil connected at its proximate end to the core wire and connected at its distal end to the tip portion of the guidewire.

In one embodiment the core wire is extended in a threadlike portion concentrically within the stainless steel coil from the distal end of the stainless steel coil to where the stainless steel coil is connected to the tip portion of the guidewire.

In another embodiment the coil defines an interior space. The interior space is free and unreinforced.

The tip portion is a long and substantially pliable segment and is comprised of a material not susceptible to electrolytic disintegration within blood.

In one embodiment the long and pliable segment has a length sufficient to substantially fill the vascular cavity when inserted therein.

In another embodiment the long and pliable segment is prebiased to form a helix when extended from the microcatheter. The helix may have a conical envelope or a cylindrical envelope.

The invention can better be visualized by now turning to the following drawings wherein like elements are referenced by like numerals.

BRIEF DESCRIPTION OF THE DRAWINGS

FIGS. 1 and 1A are enlarged partially cross-sectioned side views of a first embodiment of the distal end of the guidewire and guidewire tip of the invention.

FIGS. 2 and 2A enlarged longitudinal cross sections of a second embodiment of the guidewire and guidewire tip of the invention.

DETAILED DESCRIPTION OF THE PREFERRED EMBODIMENTS

Figure 3:
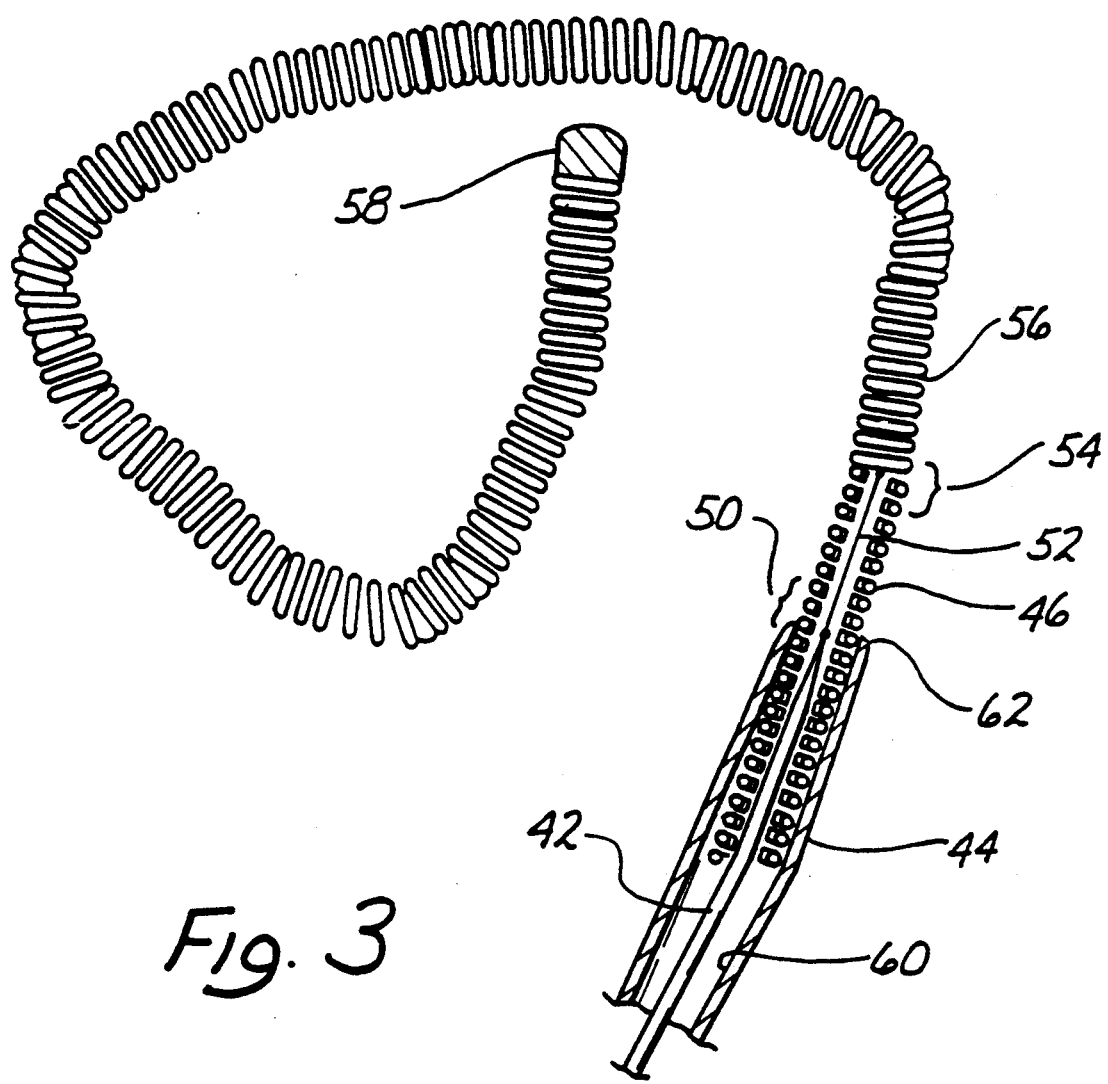
FIG. 3 is an enlarged side view of a third embodiment of the invention with a microcatheter portion cut away in a longitudinal cross-sectional view.

An artery, vein, aneurysm, vascular malformation or arterial fistula is occluded through endovascular electrothrombosis by the endovascular insertion of a platinum guidewire tip into the vascular cavity followed by application of a positive current. The guidewire tip is then separated from the guidewire by electrolytic separation of the tip from the guidewire. A portion of the guidewire connected between the tip and the body of the guidewire is comprised of stainless steel and exposed to the bloodstream so that upon continued application of a positive current to the exposed portion, the exposed portion is corroded away at least at one location and the tip is separated from the body of the guidewire. The guidewire and the microcatheter are thereafter removed leaving the guidewire tip embedded in the thrombus formed within the vascular cavity.

FIG. 1 is an enlarged side view of a first embodiment of the distal end of the guidewire and guidewire tip shown in partial cross-sectional view. A conventional Teflon laminated or similarly insulated stainless steel guidewire 10 is disposed within a protective microcatheter (not shown). Stainless steel guidewire 10 is approximately 0.010–0.020 inch (0.254–0.508 mm) in diameter. In the illustrated embodiment, guidewire 10 is tapered at its distal end to form a conical section 12 which joins a section 14 of reduced diameter which extends longitudinally along a length 16 of guidewire 10. Section 16 then narrows gradually down to a thin threadlike portion 18 beginning at a first bonding location 20 and ending at a second bonding location 22.

The stainless steel guidewire 10, comprised of that portion disposed within the microcatheter body, tapered section 12, reduced diameter section 16 and threadlike section 18, is collectively referred to as a core wire which typically is 50–300 cm. in length.

In the illustrated embodiment the portion of the core wire extending from tapered section 12 to second bonding location 22 is collectively referred to as the grinding length and may typically be between 20 and 50 cm. in length.

Reduced diameter portion 14 and at least part of sections 12 and first bonding location 20 may be covered with an insulating Teflon laminate 24 which encapsulizes the underlying portion of guidewire 10 to prevent contact with the blood.

A stainless steel coil 26 is soldered to the proximate end of threadlike portion 18 of guidewire 10 at first bonding location 20. Stainless steel coil 26 is typically 3 to 10 cm. in length and like guidewire 10 has a diameter typically between 0.010 to 0.020 inch (0.254–0.508 mm).

The distal end of stainless steel coil 26 is soldered to the distal end of threadlike portion 18 of guidewire 10 and to the proximal end of a platinum secondary coil 28 at second bonding location 22. Secondary coil 28 itself forms a spiral or helix typically between 2 to 10 mm. in diameter. The helical envelope formed by secondary coil 28 may be cylindrical or conical. Like guidewire 10 and stainless steel coil 26, secondary coil 28 is between approximately 0.010 and 0.020 inch (0.254–0.508 mm) in diameter. The diameter of the wire itself forming stainless steel coil 26 and coil 28 is approximately between 0.001–0.005 inch.

The distal end of secondary coil 28 is provided with a platinum soldered tip 30 to form a rounded and smooth termination to avoid puncturing the aneurysm or tearing tissue.

Although prebiased to form a cylindrical or conical envelope, secondary coil 28 is extremely soft and its overall shape is easily deformed. When inserted within the microcatheter (not shown), secondary coil 28 is easily straightened to lie axially within the microcatheter. Once disposed out of the tip of the microcatheter, secondary coil 28 forms the shape shown in FIG. 1 and may similarly be loosely deformed to the interior shape of the aneurysm.

As will be described below in greater detail in connection with the third embodiment of FIG. 3, after placement of secondary coil 28 within the interior of the aneurysm, a direct current is applied to guidewire 10 from a voltage source exterior to the body. The positive charge on secondary coil 28 within the cavity of the aneurysm causes a thrombus to form within the aneurysm by electrothrombosis. Detachment of the tip occurs either: (1) by continued application of current for a predetermined time when the portion 18 is exposed to blood; or (2) by movement of the wire to expose portion 18 to blood followed by continued current application for a predetermined time. Ultimately, both threadlike portion and stainless steel coil 26 will be completely disintegrated at least at one point, thereby allowing guidewire 10 to be withdrawn from the vascular space while leaving secondary coil 28 embedded within the thrombus formed within the aneurysm.

FIG. 2 illustrates in enlarged partially cross-sectional view a second embodiment of the invention. Stainless steel core 32 terminates in a conical distal portion 34.

Stainless steel coil 36, shown in cross-sectional view, is soldered to distal portion 34 of guidewire 32 at bonding location 38. The opposing end of the stainless steel coil 36 is provided with a soldered, rounded platinum tip 40. In the illustrated embodiment, stainless steel core wire 32 is approximately 0.010 inch in diameter with the length of stainless steel coil 36 being approximately 8 cm. with the longitudinal length of platinum tip 40 being between 3 and 10 mm. The total length of guidewire 32 from tip 40 to the proximate end is approximately 150 cm.

The embodiment of FIG. 2 is utilized in exactly the same manner as described above in connection with FIG. 1 to form a thrombic mass within an aneurysm or other vascular cavity. The embodiment of FIG. 2 is distinguished from that shown in FIG. 1 by the absence of the extension of stainless core 32 through coil 36 to tip 40. In the case of the embodiment of FIG. 2 no inner core or reinforcement is provided within stainless steel coil 36. Threadlike portion 18 is provided in the embodiment of FIG. 1 to allow increased tensile strength of the guidewire. However, a degree of flexibility of the guidewire is sacrificed by the inclusion even of threadlike tip 18, so that the embodiment of FIG. 2 provides a more flexible tip, at least for that portion of the microguidewire constituting the stainless steel coil 36.

It is expressly understood that the helical secondary coil tip of the embodiment of FIG. 1 could similarly be attached to stainless steel coil 36 of the embodiment of FIG. 2 without departing from the spirit and scope of the invention.

Thinned and threadlike portion guidewires disposed concentrically within coiled portions are well known and are shown in Antoshkiw, "*Disposable Guidewire*", U.S. Pat. No. 3,789,841 (1974); Sepetka et al., "*Guidewire Device*", U.S. Pat. No. 4,832,047 (1989); Engleson, "*Catheter Guidewire*", U.S. Pat. No. 4,884,579 (1989); Samson et al., "*Guidewire for Catheters*", U.S. Pat. No. 4,538,622 (1985); and Samson et al., "*Catheter Guidewire with Short Spring Tip and Method of Using the Same*", U.S. Pat. No. 4,554,929 (1985).

Turn now to the third embodiment of the invention as shown in FIG. 3. FIG. 3 shows an enlarged side view of a guidewire, generally denoted by reference numeral 42, disposed within a microcatheter 44 shown in cross-sectional view. Like the embodiment of FIG. 1, a stainless steel coil 46 is soldered to guidewire 22 at a first bonding location 50. A thin threadlike extension 52 is then longitudinally disposed within stainless steel coil 46 to a second bonding location 54 where stainless steel guidewire 46 and threadlike portion 52 are soldered to a soft platinum coil 56. Platinum coil 56 is not prebiased, nor does it contain any internal reinforcement, but is a free and open coil similar in that respect to stainless steel coil 36 of the embodiment of FIG. 2.

However, platinum coil 56 is particularly distinguished by its length of approximately 1 to 50 cm. and by its flexibility. The platinum or platinum alloy used is particularly pliable and the diameter of the wire used to form platinum coil 56 is approximately 0.001–0.005 inch in diameter. The distal end of platinum coil 56 is provided with a smooth and rounded platinum tip 58 similar in that respect to tips 30 and 40 of FIGS. 1 and 2, respectively.

When coil 56 is disposed within microcatheter 54, it lies along the longitudinal lumen 60 defined by microcatheter 44. The distal end 62 of microcatheter 60 is then placed into the neck of the aneurysm and the guidewire 42 is advanced, thereby feeding tip 58 in platinum coil 56 into aneurysm 64 until bonding location 50 resides in the neck of the aneurysm as best depicted in the diagrammatic cross-sectional view of FIG. 4.

Figure 4:
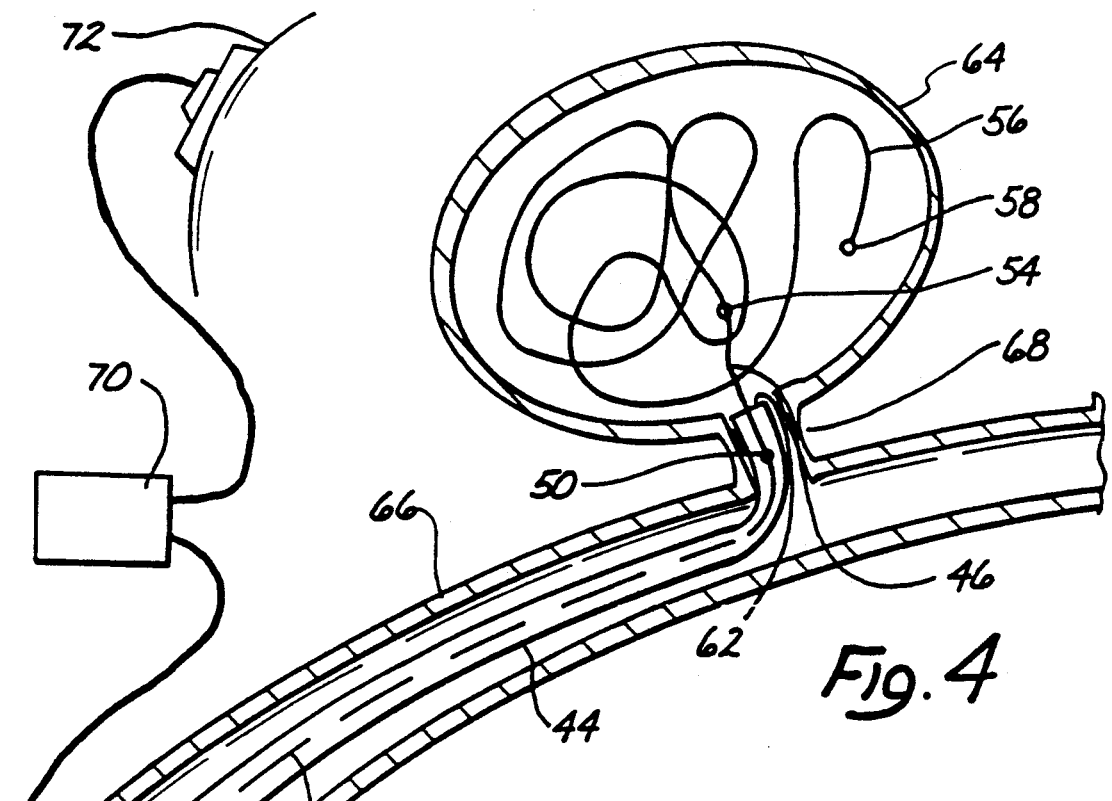
FIG. 4 is a simplified depiction of the guidewire of FIG. 3 shown disposed within a simple cranial aneurysm.

FIG. 4 illustrates the insertion of the embodiment of FIG. 3 within a vessel 66 with distal tip of microcatheter 44 positioned near neck 68 of aneurysm 64. Coil 56 is fed into aneurysm 64 until at least a portion of stainless steel coil 46 is exposed beyond the distal tip 62 of microcatheter 44. A positive electric current of approximately 0.01 to 2 milliamps at 0.1–6 volts is applied to guidewire 42 to form the thrombus. Typically a thrombus will form within three to five minutes. The negative pole 72 of voltage source 70 is typically placed over and in contact with the skin.

After the thrombus has been formed and the aneurysm completely occluded, tip 58 and coil 56 are detached from guidewire 42 by electrolytic disintegration of at least one portion of stainless steel coil 46. In the illustrated embodiment this is accomplished by continued application of current until the total time of current application is almost approximately four minutes.

Figure 5:
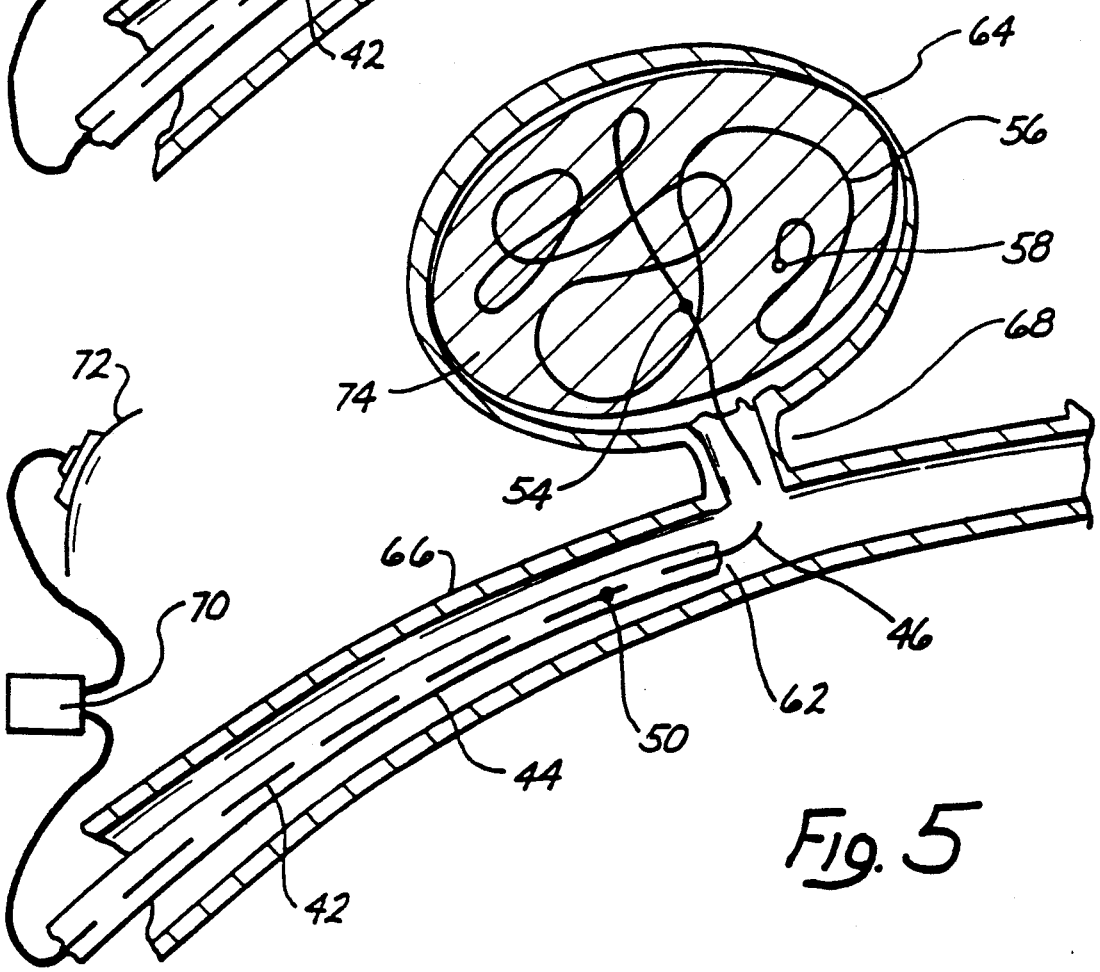
FIG. 5 is a depiction of the microguidewire of FIG. 4 shown after electrolytic detachment of the guidewire tip.

At least one portion of stainless steel coil 46 will be completely dissolved through by electrolytic action within 3 to 10 minutes, usually about 4 minutes. After separation by electrolytic disintegration, guidewire 42, microcatheter 44 and the remaining portion of coil 46 still attached to guidewire 42 are removed from vessel 66, leaving aneurysm 64 completely occluded as diagrammatically depicted in FIG. 5 by thrombus 74. It will be appreciated that the time of disintegration may be varied by altering the dimensions of the portions of the wire and/or the current.

The process is practiced under fluoroscopic control with local anesthesia at the groin. A transfemoral microcatheter is utilized to treat the cerebral aneurysm. The platinum is not affected by electrolysis and the remaining portions of the microcatheter are insulated either by a Teflon lamination directly on guidewire 42 and/or by microcatheter 44. Only the exposed portion of the guidewire 46 is affected by the electrolysis.

It has further been discovered that thrombus 74 continues to form even after detachment from guidewire 42. It is believed that a positive charge is retained on or near coil 56 which therefore continues to attract platelets, white blood cells, red blood cells and fibrinogen within aneurysm 64.

Many alterations and modifications may be made by those having ordinary skill in the art without departing from the spirit and scope of the invention. Therefore, it must be understood that the shape of the tip or distal platinum coil used in combination with the guidewire according to the invention may be provided with a variety of shapes and envelopes. In addition thereto, the composition of the microguidewire tip may be made of elements other than platinum including stainless steel, beryllium, copper and various alloys of the same with or without platinum. Still further, the diameter of the guidewire, various of the guidewire described above and the stainless steel coil immediately proximal to the detachable tip may be provided with differing diameters or cross sections to vary the times and current magnitudes necessary in order to effectuate electrolytic detachment from the tip. Still further, the invention may include conventional electronics connected to the proximal end of the guidewire for determining the exact instant of detachment of the distal tip from the guidewire.

Therefore, the illustrated embodiment has been set forth only for the purposes of clarity and example and should not be taken as limiting the invention as defined by the following claims, which include all equivalent means whether now known or later devised.

I claim:

1. A method for forming an occlusion within a vascular cavity having blood disposed therein comprising the steps of:

endovascularly disposing a guidewire near an endovascular opening into said vascular cavity;

disposing a distal tip of said guidewire into said vascular cavity to form said occlusion within said vascular cavity about said distal tip; and detaching said distal tip from said guidewire to leave said distal tip within said vascular cavity and said occlusion being formed within said vascular cavity, whereby said vascular cavity is occluded by said distal tip, and any thrombus formed by use of said tip.

2. The method of claim 1 where said step of disposing said distal tip in said vascular cavity further comprises the step of substantially occupying said vascular cavity with said distal tip.

3. The method of claim 2 where said step of substantially occupying said vascular cavity comprises the step of filling said vascular cavity with a long and pliable length of said distal tip.

4. The method of claim 1 wherein said step of detaching said distal tip from said guidewire comprises the step of electrolytically detaching said distal tip from said guidewire.

5. The method of claim 4 where said step of electrolytically detaching said distal tip from said guidewire comprises the step of electrolytically disintegrating at least one portion of a connecting segment extending between said guidewire and said distal tip.

6. The method of claim 5 where said step of electrolytically disintegrating said connecting segment comprises the step of electrolytically corroding away at least a portion of a coil segment.

7. The method of claim 6 where said step of electrolytically corroding said coil segment comprises the step of electrolytically disintegrating a stainless steel coil segment.

8. The method of claim 1 wherein said step of disposing said distal tip comprises the step of applying an electrical signal to said distal tip to form said thrombus by applying a positive direct current for a first predetermined time period.

9. The method of claim 8 wherein said step of detaching said distal tip from said guidewire comprises the step of applying a positive direct current to said distal tip for an additional predetermined time period separate from said first predetermined time period.

10. The method of claim 8 where in said step of detaching said distal tip from said guidewire, the location of detachment of said tip from said guidewire is unexposed during said first predetermined time period, and is exposed to blood during an additional predetermined time period.

11. The method of claim 1 wherein said step of detaching said distal tip from said guidewire comprises the step of applying a positive direct current to said distral tip for a predetermined time period.

12. The method of claim 1 wherein said step of disposing said tip comprises the step of disposing said guidewire in a first position relative to said vascular cavity so that a disintegratable portion of said tip remains insulated from said blood during application of a first electrical signal to said tip, and where said step of detaching comprises moving said disintegratable portion of said tip to a second position where said disintegratable portion is exposed to said blood, applying a second electrical signal to said disintegratable portion to electrolytically dissolve said disintegratable portion in said blood.

13. A guidewire for use in formation of an occlusion within a vascular cavity used in combination with a microcatheter comprising:

a core wire, said core wire having a distal portion susceptible to electrolytic distintegration in blood; and an elongate tip portion extending said core wire for a predetermined lineal extent adapted to form said occlusion in said vascular cavity and coupled to said distal portion of said core wire tip portion for endovascular insertion within a vascular cavity, said elongate tip portion not being susceptible to electrolytic disintegration in blood, whereby endovascular occlusion of said vascular cavity can be performed.

14. The guidewire of claim 13 wherein said distal portion of said core wire is an exposed stainless steel segment.

15. The guidewire of claim 14 wherein said stainless steel segment comprises a coil having a proximate and distal end, and connected at its proximate end to said core wire and connected at its distal end to said elongate tip portion of said guidewire.

16. The guidewire of claim 15 wherein said core wire is extended in a threadlike portion concentrically within said stainless steel coil from a proximal end of said stainless steel coil to where said stainless steel coil is connected to said elongate tip portion of said guidewire.

17. The guideware of claim 15 wherein said coil defines an interior space, said interior space being free and unreinforced.

18. The guideware of claim 13 wherein said elongate tip portion is a long and substantially pliable segment and is comprised of a metal not susceptible to electrolytic disintegration within blood.

19. the guidewire of claim 18 wherein said long and pliable segment of said elongate tip portion has a length sufficient to substantially fill said vascular cavity when inserted therein.

20. The guidewire of claim 13 wherein said elongate tip portion is comprised of 479 platinum alloy.

21. A guidewire for use in formation of an occlusion used in combination with a microcatheter comprising:

a core wire, said core wire having a distal portion susceptible to electrolytic disintegration in blood; and an elongate tip portion extending said core wire for a predetermined lineal extent and coupled to said distal portion of said core wire, said tip portion for endovascular insertion within a vascular cavity, said elongate tip portion not being susceptible to electrolytic disintegration in blood, wherein said elongate tip portion is a long and substantially pliable segment and is comprised of a mental not susceptible to electrolytic disintegration within blood, and wherein said long and pliable segment is prebiased to form a helix when extended from said microcatheter, whereby endovascular occlusion of said vascular cavity can be performed.

22. the guidewire of claim 21 wherein said helix has a conical envelope.

23. The guidewire of claim 21 wherein said helix has a cylindrical envelope.

* * * * *

UNITED STATES PATENT AND TRADEMARK OFFICE
CERTIFICATE OF CORRECTION

PATENT NO. : 5,122,136
DATED : June 16, 1992
INVENTOR(S) : Guido Guglielmi and Ivan Sepetka It is certified that error appears in the above-indentified patent and that said Letters Patent is hereby corrected as shown below:

In Claim 11, col. 9, line 61, delete "distral" and insert --distal--.

In Claim 13, col. 10, line 14, after "said core wire" and before "tip portion", insert --, said--.

In Claims 17 and 18, col. 10, lines 33 and 35 delete "guideware" and insert --guidewire--.

In Claim 21, col. 10, line 58, delete "mental" and insert --metal--.

Signed and Sealed this

Fifth Day of December, 1995

*Attest:*

BRUCE LEHMAN

*Attesting Officer*   *Commissioner of Patents and Trademarks*

(12) EX PARTE REEXAMINATION CERTIFICATE (5527th)
United States Patent
Guglielmi et al.

(10) Number: US 5,122,136 C1
(45) Certificate Issued: Sep. 26, 2006

(54) ENDOVASCULAR ELECTROLYTICALLY DETACHABLE GUIDEWIRE TIP FOR THE ELECTROFORMATION OF THROMBUS IN ARTERIES, VEINS, ANEURYSMS, VASCULAR MALFORMATIONS AND ARTERIOVENOUS FISTULAS

(75) Inventors: Guido Guglielmi, Los Angeles, CA (US); Ivan Sepetka, Redwood City, CA (US)

(73) Assignee: The Regents of the University of California, Oakland, CA (US)

Reexamination Request:
No. 90/007,230, Oct. 4, 2004

Reexamination Certificate for:
Patent No.: 5,122,136
Issued: Jun. 16, 1992
Appl. No.: 07/492,717
Filed: Mar. 13, 1990

Certificate of Correction issued Dec. 5, 1995.

(51) Int. Cl.
   *A61B 18/12* (2006.01)

(52) U.S. Cl. ............................ 606/32; 606/41; 604/907; 600/585

(58) Field of Classification Search ................... 606/32, 606/41; 604/97; 600/585
See application file for complete search history.

(56) References Cited

U.S. PATENT DOCUMENTS

| | | |
|---|---|---|
| 3,334,629 A | 8/1967 | Cohn |
| 3,452,742 A | 7/1969 | Muller |
| 3,521,620 A | 7/1970 | Cook |
| 3,547,103 A | 12/1970 | Cook |
| 3,605,750 A | 9/1971 | Sheridan et al. |
| 3,773,034 A | 11/1973 | Burns et al. |
| 3,789,841 A | 2/1974 | Antoshkiw |
| 3,868,956 A | 3/1975 | Alfidi et al. |
| 3,952,747 A | 4/1976 | Kimmell, Jr. |
| 3,996,938 A | 12/1976 | Clark, III |
| 4,003,369 A | 1/1977 | Heilman et al. |
| 4,080,706 A | 3/1978 | Heilman et al. |
| 4,114,603 A | 9/1978 | Wilkinson |
| 4,147,169 A | 4/1979 | Taylor |
| 4,190,057 A | 2/1980 | Hill et al. |
| 4,213,461 A | 7/1980 | Pevsner |

(Continued)

FOREIGN PATENT DOCUMENTS

AT    0197237 E    3/2001

(Continued)

OTHER PUBLICATIONS

Guerrisi R., Guglielmi G. et al., "*L'elettrotrombosi intravasale nelle malformazioni vascolari sperimentalmente provate* (Intravascular Electrothrombosis in Experimentally Induced Vascular Malformations)," In: Proceedings of III Congress of the Italian Society of Neuroradiology, Bari 1983, pp. 139–146 (and original translation provided to PTO by applicant).

(Continued)

*Primary Examiner*—Michael O'Neill

(57) ABSTRACT

An artery, vein, aneurysm, vascular malformation or arterial fistula is occluded through endovascular electrothrombosis by the endovascular insertion of a platinum guidewire tip into the vascular cavity followed by application of a positive current. The guidewire tip is then separated from the guidewire by electrolytic separation of the tip from the guidewire. A portion of the guidewire connected between the tip and the body of the guidewire is comprised of stainless steel and exposed to the bloodstream so that upon continued application of a positive current to the exposed portion, the exposed portion is corroded away at least at one location and the tip is separated from the body of the guidewire. The guidewire and the microcatheter are thereafter removed leaving the guidewire tip embedded in the thrombus formed within the vascular cavity.

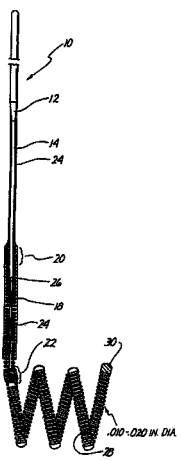

U.S. PATENT DOCUMENTS

| | | |
|---|---|---|
| 4,323,071 A | 4/1982 | Simpson et al. |
| 4,327,734 A | 5/1982 | White, Jr. |
| 4,341,218 A | 7/1982 | U |
| 4,346,712 A | 8/1982 | Handa et al. |
| 4,402,319 A | 9/1983 | Handa et al. |
| 4,411,648 A | 10/1983 | Davis et al. |
| 4,413,989 A | 11/1983 | Schjeldahl et al. |
| 4,512,338 A | 4/1985 | Balko et al. |
| 4,517,979 A | 5/1985 | Pecenka |
| 4,522,205 A | 6/1985 | Taylor et al. |
| 4,538,622 A | 9/1985 | Samson et al. |
| 4,545,367 A | 10/1985 | Tucci |
| 4,545,390 A | 10/1985 | Leary |
| 4,554,929 A | 11/1985 | Samson et al. |
| 4,576,174 A | 3/1986 | Miyazaki et al. |
| 4,597,389 A | 7/1986 | Ibrahim et al. |
| 4,613,324 A | 9/1986 | Morrison |
| 4,619,274 A | 10/1986 | Morrison |
| RE32,348 E | 2/1987 | Pevsner |
| 4,641,654 A | 2/1987 | Samson et al. |
| 4,655,746 A | 4/1987 | Daniels et al. |
| 4,660,571 A | 4/1987 | Hess et al. |
| 4,669,465 A | 6/1987 | Moore et al. |
| 4,682,596 A | 7/1987 | Bales et al. |
| 4,723,556 A | 2/1988 | Sussman |
| 4,729,914 A | 3/1988 | Kliment et al. |
| 4,735,201 A | 4/1988 | O'Reilly |
| 4,739,768 A | 4/1988 | Engelson |
| 4,748,986 A | 6/1988 | Morrison et al. |
| 4,782,834 A | 11/1988 | Maguire et al. |
| 4,787,899 A | 11/1988 | Lazarus |
| 4,793,359 A | 12/1988 | Sharrow |
| 4,800,882 A | 1/1989 | Gianturco |
| 4,813,934 A | 3/1989 | Engelson et al. |
| 4,820,298 A | 4/1989 | Leveen et al. |
| 4,821,722 A | 4/1989 | Miller et al. |
| 4,830,003 A | 5/1989 | Wolff et al. |
| 4,832,047 A | 5/1989 | Sepetka et al. |
| 4,838,268 A | 6/1989 | Keith et al. |
| 4,838,879 A | 6/1989 | Tanabe et al. |
| 4,878,906 A | 11/1989 | Lindemann et al. |
| 4,884,579 A | 12/1989 | Engelson |
| 4,907,336 A | 3/1990 | Gianturco |
| 4,917,088 A | 4/1990 | Crittenden |
| 4,943,278 A | 7/1990 | Euteneuer et al. |
| 4,944,746 A | 7/1990 | Iwata et al. |
| 4,950,239 A | 8/1990 | Gahara et al. |
| 4,968,306 A | 11/1990 | Huss et al. |
| 4,969,458 A | 11/1990 | Wiktor |
| 4,986,830 A | 1/1991 | Owens et al. |
| 4,989,608 A | 2/1991 | Ratner |
| 4,991,069 A | 2/1991 | Tiller |
| 4,994,069 A | 2/1991 | Ritchart et al. |
| 4,998,933 A | 3/1991 | Eggers et al. |
| 5,002,556 A | 3/1991 | Ishida et al. |
| 5,011,482 A | 4/1991 | Goode et al. |
| 5,019,075 A | 5/1991 | Spears et al. |
| 5,021,043 A | 6/1991 | Becker et al. |
| 5,041,090 A | 8/1991 | Scheglov et al. |
| 5,055,101 A | 10/1991 | McCoy |
| 5,061,914 A | 10/1991 | Busch et al. |
| 5,102,390 A | 4/1992 | Crittenden et al. |
| 5,104,376 A | 4/1992 | Crittenden |
| 5,108,407 A | 4/1992 | Geremia et al. |
| 5,108,416 A | 4/1992 | Ryan et al. |
| RE33,925 E | 5/1992 | Bales et al. |
| 5,109,867 A | 5/1992 | Twyford, Jr. |
| 5,116,652 A | 5/1992 | Alzner |
| 5,122,136 A | 6/1992 | Guglielmi et al. |
| 5,133,731 A | 7/1992 | Butler et al. |
| 5,135,516 A | 8/1992 | Sahatjian et al. |
| 5,143,085 A | 9/1992 | Wilson |
| 5,147,315 A | 9/1992 | Weber |
| 5,154,179 A | 10/1992 | Ratner |
| 5,167,624 A | 12/1992 | Butler et al. |
| 5,169,386 A | 12/1992 | Becker et al. |
| 5,171,233 A | 12/1992 | Amplatz et al. |
| 5,171,297 A | 12/1992 | Barlow et al. |
| 5,178,618 A | 1/1993 | Kandarpa |
| 5,180,368 A | 1/1993 | Garrison |
| 5,188,621 A | 2/1993 | Samson |
| 5,191,297 A | 3/1993 | Penman et al. |
| 5,201,323 A | 4/1993 | Vermeulen |
| 5,201,754 A | 4/1993 | Crittenden et al. |
| 5,209,730 A | 5/1993 | Sullivan |
| 5,217,484 A | 6/1993 | Marks |
| 5,226,911 A | 7/1993 | Chee et al. |
| 5,234,437 A | 8/1993 | Sepetka |
| 5,242,396 A | 9/1993 | Evard |
| 5,246,421 A | 9/1993 | Saab |
| 5,250,071 A | 10/1993 | Palermo |
| 5,254,130 A | 10/1993 | Poncet et al. |
| 5,261,916 A | 11/1993 | Engelson |
| 5,263,964 A | 11/1993 | Purdy |
| 5,275,594 A | 1/1994 | Baker et al. |
| 5,304,195 A | 4/1994 | Twyford et al. |
| 5,306,287 A | 4/1994 | Becker |
| 5,312,415 A | 5/1994 | Palermo |
| 5,334,210 A | 8/1994 | Gianturco |
| 5,342,294 A | 8/1994 | Wiest et al. |
| 5,342,387 A | 8/1994 | Summers |
| 5,345,927 A | 9/1994 | Bonutti |
| 5,350,397 A | 9/1994 | Palermo et al. |
| 5,354,295 A | 10/1994 | Guglielmi et al. |
| 5,360,443 A | 11/1994 | Barone et al. |
| 5,382,261 A | 1/1995 | Palmaz |
| 5,423,829 A | 6/1995 | Pham et al. |
| 5,449,372 A | 9/1995 | Schmaltz et al. |
| 5,454,826 A | 10/1995 | Ueda |
| 5,522,836 A | 6/1996 | Palermo |
| 5,540,680 A | 7/1996 | Guglielmi et al. |
| 5,569,245 A | 10/1996 | Guglielmi et al. |
| 5,609,608 A | 3/1997 | Benett et al. |
| 5,645,558 A | 7/1997 | Horton |
| 5,645,564 A | 7/1997 | Northrup et al. |
| 5,690,668 A | 11/1997 | Engelson et al. |
| 5,718,711 A | 2/1998 | Berenstein et al. |
| 5,724,534 A | 3/1998 | Boursier et al. |
| 5,725,552 A | 3/1998 | Kotula et al. |
| 5,733,294 A | 3/1998 | Forber et al. |
| 5,743,905 A | 4/1998 | Eder et al. |
| 5,766,219 A | 6/1998 | Horton |
| 5,797,953 A | 8/1998 | Tekulve |
| 5,800,454 A | 9/1998 | Jacobsen et al. |
| 5,814,062 A | 9/1998 | Sepetka et al. |
| 5,826,587 A | 10/1998 | Berenstein et al. |
| 5,851,206 A | 12/1998 | Guglielmi et al. |
| 5,855,578 A | 1/1999 | Guglielmi et al. |
| 5,882,334 A | 3/1999 | Sepetka et al. |
| 5,891,128 A | 4/1999 | Gia et al. |
| 5,891,130 A | 4/1999 | Palermo et al. |
| 5,891,155 A | 4/1999 | Irie |
| 5,895,385 A | 4/1999 | Guglielmi et al. |
| 5,895,391 A | 4/1999 | Farnholtz |
| 5,911,717 A | 6/1999 | Jacobsen et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,062 A | 7/1999 | Purdy |
| 5,928,226 A | 7/1999 | Guglielmi et al. |
| 5,944,714 A | 8/1999 | Guglielmi et al. |

| | | | | | | |
|---|---|---|---|---|---|---|
| 5,944,733 | A | 8/1999 | Engelson | EP | 0366407 A2 | 5/1990 |
| 5,947,962 | A | 9/1999 | Guglielmi et al. | EP | 0366407 A3 | 5/1990 |
| 5,947,963 | A | 9/1999 | Guglielmi | EP | 0471754 | 5/1990 |
| 5,972,019 | A | 10/1999 | Engelson et al. | EP | 0 397 357 A1 | 11/1990 |
| 5,976,126 | A | 11/1999 | Guglielmi | EP | 0 422 632 A2 | 4/1991 |
| 5,976,131 | A | 11/1999 | Guglielmi et al. | EP | 0442657 A2 | 8/1991 |
| 5,980,514 | A | 11/1999 | Kupiecki et al. | EP | 0516717 | 9/1991 |
| 6,010,498 | A | 1/2000 | Guglielmi | EP | 0471683 | 1/1992 |
| 6,066,133 | A | 5/2000 | Guglielmi et al. | EP | 0220285 B1 | 7/1992 |
| 6,083,220 | A | 7/2000 | Guglielmi et al. | EP | 0493878 A2 | 7/1992 |
| 6,096,034 | A | 8/2000 | Kupiecki et al. | EP | 0493878 A3 | 7/1992 |
| 6,168,592 | B1 | 1/2001 | Kupiecki et al. | EP | 0494495 A1 | 7/1992 |
| 6,168,615 | B1 | 1/2001 | Ken et al. | EP | 0495861 B1 | 5/1993 |
| 6,238,415 | B1 | 5/2001 | Sepetka et al. | EP | 0484468 A4 | 3/1994 |
| 6,344,041 | B1 | 2/2002 | Kupiecki et al. | EP | 0375775 B1 | 8/1994 |
| 6,425,893 | B1 | 7/2002 | Guglielmi | EP | 0629125 A1 | 5/1995 |
| 6,468,266 | B1 | 10/2002 | Bashiri et al. | EP | 0484486 B1 | 1/1996 |
| 6,620,152 | B1 | 9/2003 | Guglielmi | EP | 0707830 A1 | 4/1996 |
| 2002/0151883 | A1 | 10/2002 | Guglielmi | EP | 0750886 A1 | 1/1997 |

FOREIGN PATENT DOCUMENTS

| | | | | | |
|---|---|---|---|---|---|
| EP | 0 804 906 A3 | 5/1997 | | | |
| EP | 0 800 790 A3 | 10/1997 | | | |
| AU | 591906 | 11/1986 | EP | 0 800 790 A2 | 10/1997 |
| AU | 58652/86 | 11/1986 | EP | 0 803 230 A2 | 10/1997 |
| AU | 621923 | 11/1989 | EP | 0 803 230 A3 | 11/1997 |
| AU | 39345/89 A | 11/1989 | EP | 0 804 904 A1 | 11/1997 |
| AU | 0636217 B2 | 10/1991 | EP | 0 804 905 A1 | 11/1997 |
| AU | 74474/91 | 10/1991 | EP | 0 629 125 B1 | 6/1998 |
| AU | 0673502 B2 | 9/1993 | EP | 0 804 906 B1 | 1/1999 |
| AU | 704583 | 5/1996 | EP | 0587782 B1 | 4/1999 |
| AU | 34291/95 | 5/1996 | EP | 0914803 A1 | 5/1999 |
| AU | 0723902 B2 | 1/1997 | EP | 0 484 468 B1 | 6/1999 |
| AU | 56244/96 | 1/1997 | EP | 0 800 790 B1 | 7/1999 |
| CA | 1308988 | 10/1992 | EP | 0 804 905 B1 | 7/1999 |
| CA | 2160640 | 4/1996 | EP | 1 005 837 A3 | 6/2000 |
| CA | 2179863 | 12/1996 | EP | 1 005 837 A2 | 6/2000 |
| CA | 2055492 C | 11/2000 | EP | 0 803 230 B1 | 11/2000 |
| CA | 20554492 C | 11/2000 | EP | 0 707 830 B1 | 2/2001 |
| DD | 158.084 | 12/1982 | EP | 0750886 B1 | 4/2003 |
| DD | 223 065 A1 | 6/1985 | EP | 1 005 837 B1 | 4/2003 |
| DE | 3 203 410 | 11/1982 | EP | 0 914 803 B1 | 7/2003 |
| DE | 3334174 C2 | 3/1984 | EP | 1 323 385 A2 | 7/2003 |
| DE | 3334174 A1 | 3/1984 | EP | 1 323 385 A3 | 7/2003 |
| DE | 3690224 T1 | 8/1987 | EP | 1 329 196 A1 | 7/2003 |
| DE | 69001759 T2 | 1/1994 | FI | 9615332 | 11/1991 |
| DE | 3690224 C2 | 11/1998 | FI | 941937 | 6/1994 |
| DE | 69226024 T2 | 1/1999 | GB | 2185190 A | 7/1987 |
| DE | 69228134 T2 | 5/1999 | GB | 2208607 A | 4/1989 |
| DE | 69131340 T2 | 10/1999 | GB | 2245495 A | 1/1992 |
| DE | 69131466 T2 | 11/1999 | HU | 219694 B | 1/1991 |
| DE | 69131467 T2 | 11/1999 | HU | 0913536 | 1/1991 |
| DE | 69231550 T2 | 6/2001 | IL | 115609 | 10/1995 |
| DE | 69520186 T2 | 6/2001 | IL | 0115609 | 10/1995 |
| DE | 69233026 T2 | 1/2004 | IT | 1224838 | 10/1990 |
| DE | 69627243 T2 | 1/2004 | JP | 62-502950 | 11/1987 |
| DE | 69133297 T2 | 6/2004 | JP | 5-500322 | 1/1993 |
| DK | 0803230 | 10/1997 | JP | 5-38366 | 2/1993 |
| EP | 0 117 940 A2 | 9/1984 | JP | 5-23153 | 3/1993 |
| EP | 0 119 688 A2 | 9/1984 | JP | 6-26576 | 4/1994 |
| EP | 0058708 B1 | 5/1985 | JP | 7-503165 | 4/1995 |
| EP | 0220285 | 11/1986 | JP | 2501389 | 3/1996 |
| EP | 0212936 A1 | 3/1987 | JP | 8-196544 | 8/1996 |
| EP | 0249371 A2 | 12/1987 | JP | 9-98981 | 4/1997 |
| EP | 0249371 A3 | 12/1987 | JP | 3131386 | 11/2000 |
| EP | 0253620 A2 | 1/1988 | JP | 3152399 | 1/2001 |
| EP | 0253620 A3 | 1/1988 | KR | 10-0200441 | 8/1999 |
| EP | 0255331 A3 | 2/1988 | NO | 914433 | 1/1992 |
| EP | 0255331 A2 | 2/1988 | NO | 943106 | 8/1994 |
| EP | 0296224 | 6/1988 | NO | 962745 | 1/1997 |
| EP | 0296224 | 3/1989 | PT | 101162 | 12/1992 |
| EP | 0220285 | 11/1989 | WO | WO 82/00768 | 3/1982 |
| EP | 0471683 | 4/1990 | WO | WO 84/04686 | 12/1984 |

| | | |
|---|---|---|
| WO | WO 86/06285 | 11/1986 |
| WO | WO 87/00062 | 1/1987 |
| WO | WO 88/01851 | 3/1988 |
| WO | WO 90/01840 | 2/1990 |
| WO | WO 90/02585 | 3/1990 |
| WO | WO 91/13592 | 1/1991 |
| WO | WO 91/04716 | 4/1991 |
| WO | WO 92/01425 | 2/1992 |
| WO | WO 92/08342 | 5/1992 |
| WO | WO 92/14408 | 9/1992 |
| WO | WO 92/21400 | 12/1992 |
| WO | WO 93/11825 | 6/1993 |
| WO | WO 93/16650 | 9/1993 |
| WO | WO 94/06503 | 3/1994 |
| WO | WO 94/10936 | 5/1994 |
| WO | WO 95/23558 | 9/1995 |
| WO | WO 95/25480 | 9/1995 |
| WO | WO 97/48351 | 12/1997 |
| WO | WO 98/02100 | 1/1998 |
| WO | WO 98/04195 | 2/1998 |
| WO | WO 98/04196 | 2/1998 |
| WO | WO 98/04198 | 2/1998 |
| WO | WO 98/04315 | 2/1998 |
| WO | WO 01/32085 A1 | 5/2001 |
| WO | WO 02/14408 | 2/2002 |
| WO | WO 03/017852 A1 | 3/2003 |
| ZA | 81-2814 | 4/1981 |

OTHER PUBLICATIONS

Guerrisi R., Guglielmi G. et al., "*L'elettrotrombosi intravasale nelle malformazioni vascolari sperimentalmente provocate* (Intravascular Electrothombosis in Experimentally Induced Vascular Malformations)," In: Proceedings of III Congress of the Italian Society of Neuroradiology, Bari 1983, pp. 139–146 (and certified translation provided by Quest Technology).

Guglielmi, Guido, "Endovascular Occlusion of Aneurysms by Electrothrombosis," U.S. Department of Health and Human Services Grant Application No: 1 RO1 HL46286–01, (May 22, 1990) ("1990 NIH Grant Request").

G. Guglielmi et al., "Endovascular occlusion by electrothrombosis of experimental small and medium–sized saccular aneurysms," 28$^{th}$ Annual Meeting of ASNR, Mar. 19–23, 1990.

Guglielmi G. et al., "Electrthrombosis of saccular aneurysms via endovascular approach, Part 1: Electrochemical basis, technique, and experimental results," *Journal of Neurosurgery,* 75:1–7 (Jul. 1991).

Guglielmi G. et al., "Electrothrombosis of saccular aneurysms via endovascular approach, Part 2: Preliminary clinical experience," *Journal of Neurosurgery,* 75:8–14 (Jul. 1991).

Guglielmi G. et al., "Endovascular treatment of posterior circulation aneurysms by electrothrombosis using electrically detachable coils," *Journal of Neurosurgery,* 77:515–524 (Oct. 1992).

Castaneda–Zuniga, "A New Device for the Safe Delivery of Stainless Steel Coils," *Radiology,* 136:230–31 (Jul. 1980).

Anderson, "Transcatheter Intravascular Coil Occlusion of Experimental Arteriovenous Fistulas," in the *American Journal of Roentgenology,* vol. 129, p. 795–98 (Nov. 1977).

Taki et al., "The Releasable Balloon Technique With Activated High Frequency Electrical Current," *Surgical Neurology,* 13:405–08 (Jun. 1980).

Hawkins, Retrievable Gianturco–Coil Introducer, *Radiology,* 158:262–64 (Jan. 1986).

Taki et al., "Detachable Balloon Catheter Systems for Embolization of Cerebrovascular Lessions," *Neuro. Med. Chir. (Tokyo),* 21:709–19 (1981).

Anderson et al., "'Mini' Gianturco Stainless Steel Coils for Transcatheter Vascular Occlusion," *Radiology* 132:301–03 (Aug. 1979).

O'Reilly et al., "Laser–induced Thermal Occlusion of Berry Aneurysims: Initial Experimental Results," *Radiology* 171:471–74 (May 1989).

Abramson, H.A., "A Possible Relationship Between The Current Of Injury And The White–Blood Cell Inflamation," American J. Medical Sciences, 1924, pp. 702–711, vol. CLXVII.

"All Things Considered," of NPR, Jun. 28, 2000, Hour 1, pp. 10–20.

Almgard, L.E. et al., "Embolic Occlusion Of An Intrarenal Aneurysm: A Case Report," British Journal Of Urology, 1973, pp. 485–488, vol. 45.

"Amendment in 07/492,717," Aug. 7, 1991, pp. 8.

"Amendment Under 37 C.F.R. § 1.111 in 08/147,529," Jun. 30, 1994, pp. 1–12.

Amplatz, K., "A New, Simple Test For Thrombogenicity," Radiology, Jul.–Sep. 1976, pp. 53–55, vol. 120.

Amplatz, K., "Vessel Occlusion With Transcatheter Electrocoagulation: Negative Results," pp. 253–255.

Anderson, J. H. et al., "'Mini' Gianturco Stainless Steel Coils For Transcatheter Vascular Occlusion," Radiology, Aug. 1979, pp. 301–303, vol. 132, No. 2.

Araki, C. et al., "Electrically Induced Thrombosis For The Treatment Of Intracranial Aneurysms And Angiomas," Proceedings of the Third International Congress of Neurological Surgery, Aug. 23–27, 1965, pp. 651–654.

Auger, R. G. et al., "Management Of Unruptured Intracranial Aneurysms," J. Stroke Cerebrovasc. Dis., 1991, pp. 174–181, vol. 1, No. 4.

Ausman, J. I. et al., "Current Management Of Cerebral Aneurysms: Is It Based On Facts Or Myths?" Surg. Neurol., 1985, pp. 625–634, vol. 24.

Barth, K. H. et al., "Chronic Vascular Reaction To Steel Coil Occlusion Devices," Am. J. Roentgenol., Sep. 1978, pp. 455–458, vol. 131.

Bavinzski, G. et al., "Gross And Microscopic Histopathological Findings In Aneurysms Of The Human Brain Treated With Guglielmi Detachable Coils," J. Neurosurg., Jul. 1999, pp. 284–293, vol. 91, No. 1.

Bendok, B. et al., "Coil Embolization Of Intracranial Aneurysms," Neurosurgery, May 2003, pp. 1125–1130, vol. 52, No. 5.

Berenstein, A., "Embolization Of Spinal Cord AVMS," 4 pages.

Berenstein, A., "Tissue Response To Guglielmi Detachable Coils: Present Implications And Future Developments," AJNR, Apr. 1999, vol. 20.

Billmeyer, F.W., "Textbook Of Polymer Science," 1961, pp. 108–113.

Blakemore, A. H. et al., "Electrothermic Coagulation Of Aortic Aneurysms," The Journal Of The American Medical Association, Oct. 1, 1938, pp. 1821–1827, vol. III, No. 20.

Blakemore, A.H., "Progressive Constrictive Occlusion Of The Abdominal Aorta With Wiring And Electrothermic Coagulation," Annals of Surgery, Jan.–Jun. 1951, pp. 447–462, vol. 133.

Brendler, H. "Early Days of Urology At Mount Sinai," Urology, Jun. 1974, pp. 246–250, vol. III, No. 6.

Brunelle, F. et al., "A Bipolar Electrode For Vascular Electrocoagulation With Alternating Current," Radiology, Oct.–Dec. 1980, pp. 239–240, vol. 137.

Brunelle, F. et al., "'Micro' Stainless Steel Coils For Transcatheter Vascular Occlusion in Children," Pediatr. Radiol., 1983, pp. 332–334, vol. 13.

Bursch, J. H. et al., "Assessment Of Arterial Blood Flow Measurement By Digital Angiography," Radiology, Oct. 1981, pp. 39–47, vol. 141.

Butto, F. et al., "Coil–In–Coil Technique For Vascular Embolization," Radiology, Nov. 1986, pp. 554–555, vol. 161.

Casasco, A. et al., "Percutaneous Transvenous Catheterization And Embolization Of Vein Of Galen Aneurysms," Neurosurgery, 1991, pp. 260–266, vol. 28.

Casasco, A. E. et al., "Selective Endovascular Treatment Of 71 Intracranial Aneurysms With Platinum Coils," J. Neurosurg., 1993, pp. 3–10, vol. 79.

Castaneda–Zuniga, W. R. et al., "Experimental Venous Occlusion With Stainless Steel Spiders," Radiology, Oct.–Dec. 1981, pp. 238–242, vol. 141.

Castaneda–Zuniga, W. R. et al., "Nonsurgical Closure Of Large Arteriovenous Fistulas," JAMA, Dec. 6, 1976, pp. 2649–2650, vol. 236, No. 23.

Castaneda–Zuniga, W.R. et al., "A Rare Source Of Pulmonary Embolization In Catheterization Procedures," Radiology, Oct.–Dec. 1981, pp. 237–242, vol. 141.

Castaneda–Zuniga, W. R. et al., "Single Barbed Stainless Steel Coils For Venous Occlusion A Single But Useful Modification," Investigative Radiology, Mar.–Apr. 1982, pp. 186–188, vol. 17, No. 2.

Castaneda–Zuniga, W. R. et al., "Therapeutic Embolization Of Facial Arteriovenous Fistulae," Radiology, Jul.–Sep. 1979, pp. 599–602, vol. 132.

Castel, J. C. et al., "Les Anevrysmes <<Hypergeants>> Intracraniens Sus–Tentoriels—Pieges Diagnostiques," J. Neuroradiology, 1985, pp. 135–149, vol. 12.

Castro, E. et al., "Long–Term Histopathologic Findings in Two Cerebral Aneurysms Embolized With Guglielemi Detachable Coils," AJRN, Apr. 1999, pp. 549–552, vol. 20.

Choi, I., "Spinal Cord Tumors," pp. 57–61.

Chuang, V. P. et al., "A New Improved Coil For Tapered–Tip Catheter For Arterial Occlusion," Radiology, May 1980, pp. 507–509, vol. 135.

Davis, P., "Southeastern Neuroradiological Society: 15th Annual Meeting, Oct. 2–8, 1991, Williamsburg, VA." AJNR, May/Jun. 1992, p. 1038, vol. 13.

Debrun, G., "Dural AVM's Of The Cavernous Sinus Region: Clinical Presentation, Angiographic Evaluation, Embolization And Complications," 2 pages.

de los Reyes, R. A. et al., "Transcallosal, Transventricular Approach To A Basilar Apex Aneurysm," Neurosurgery, Sep. 1992, p. 397, vol. 31, No. 3.

"Dendron Electrolytically Detachable Coils," Dendron GmbH, pp. 1–5, & Jul. 23, 2001.

"Dendron Electrolytically Detachable Coil (EDC II) Package Info.," 8 pages.

"Dendron New Positioning System for the EDC II and VDS: Technical Note," 2 pages.

"Device For The Implantation Of Occlusion Means," pp. 1–27.

Disclosure Of Expert Testimony Of Dr. Randall T. Higashida Under Fed. R. Cly. P. 26(A)(2), 198 pages.

Eskridge, J. M. et al., "Endovascular Embolization Of 150 Basilar Tip Aneurysms With Guglielmi Detachable Coils: Results Of The Food And Drug Administration Multicenter Clinical Trial," J. Neurosurg., Jul. 1998, pp. 81–86, vol. 89.

Formanek, A. et al., "Transcatheter Embolization (Interventive Radiology) In The Pediatric Age Group And Adolescent," Annales De Radiologie Medecine Nuceaire, Jan.–Feb. 1979, pp. 150–159, No. 1.

Fox, A., "Highlights Of The First Congress Of The World Federation Of Interventional And Therapeutic Neuroradiology, Oct. 11–13, 1991, Zurich, Switzerland," pp. 1021–1023.

Fox, A., "Notes On The Working Group In Interventional Neuroradiology," AJNR, Jan. 13–20, 1990, pp. 840–841, vol. 11.

Frazer, H., "Balloons And Electricity: Treating Brain Aneurysms," Diagnostic Imaging, Jul. 1990, pp. 115–117.

Gangarosa, E.J. et al., "Ristocetin–Induced Thrombocytopenia: Site And Mechanism Of Action," A.M.A. Archives Of Internal Medicine, 1960, pp. 83–89, vol. 105.

Gelfand, D. W. et al., "Gastric Ulcer Scars," Radiology, Jul. 1981, pp. 37–43, vol. 140, No. 1.

Gibbs, J., "Medical Device Investigations Understanding IRB And Informed Consent Requirements," Medical Device & Diagnostic Industry, Jun. 1989, pp. 103–106.

Gold, R. F. et al., "Transarterial Electrocoagulation Therapy Of A Pseudoaneurysm In The Head Of The Pancreas," Oct. 1975, pp. 422–426.

Goldman, M. L. et al., "Transcatheter Embolization With Bucrylate (In 100 Patients)," RadioGraphics, Aug. 1982, pp. 340–375, vol. 2, No. 3.

Gomes, A.S. et al., "The Use Of The Bristle Brush For Transcatheter Embolization," Radiology, Nov. 1978, pp. 345–350, vol. 129.

Groeneveld, Y. G., "Rapport Inzake EP–484.468 & EP–800.790 & EP–804.905 Niet–inbreuk & Ongeldigheid," 43 pages.

Guarda, F. et al., "Histological Reactions Of Porous Tip Endocardial Electrodes Implanted In Sheep," pp. 267–273.

Guglielmi, G. et al., "Carotid–Cavernous Fistula Caused By A Ruptured Intracavernous Anuerysm: Endovascular Treatment By Electrothrombosis With Detachable Coils," Neurosurgery, Sep. 1992, pp. 591–597, vol. 31, No. 3.

Guglielmi, G. et al., "Electrothrombosis Of Saccular Aneurysms Via Endovascular Approach, Part 2" J. Neurosurg., 1991, pp. 8–14, vol. 75.

Guglielmi, G., "Endovascular Treatment Of Intracranial Aneurysms," Interventional Neuroradiology, May 1992, pp. 269–278, vol. 2, No. 2.

Guglielmi, G. et al., "Endovascular Treatment Of Intracranial Saccular Aneurysms With Detachable Coils And Electrothrombosis: Experience With 39 Cases," 1992 AANS Annual Meeting San Francisco, CA, Apr. 11–16, 1992.

Guglielm, G., "In Re: Radiologic And Histopathology Evaluation Of Canine Artery Occlusion After Collagen–Coated Platinum Microcoil Delivery," Letters, p. 607.

Guglielmi, G., "Generations Of Guglielmi Detachable Coils," AJNR, Jun. 1997, p. 1195, vol. 16.

Gyo, K., "Histological Study Of Chronic Electrode Implantation Through The Round Window Of The Guinea Pig," Acta Ototaryngol (Stockh), 1988, pp. 248–254, vol. 105.

Halbach, V. V. et al., "Embolization Of Brain AVMS With Particles," 4 pages.

Halbach, V. V. et al., "Paper 221: Metallic Fragment Emboli Resulting From Treatment With Electrolytically Detachable Coils (GDC)," Proceedings of the American Society Of Neuroradiology (ASNR), May 3–7, 1994, pp. 155–156.

Xinan, H. "Transcatheter Electrocoagulation: A Preliminary Experimental Study," Chinese Journal of Radiology, Apr. 1987, pp. 241–245.

Xinan, H. et al., "Vascular Embolization Utilizing Transcatheter Electrocoagulation In Combination With Steel Coil: An Experimental Study," Chinese Journal of Radiology, Mar. 1988, pp. 180–183.

Han, M. et al., "Gas Generation And Clot Formation During Electrolytic Detachment Of Guglielmi Detachable Coils: In Vitro Observations And Animal Experiment," AJNR, Mar. 2003, pp. 539–544, vol. 24.

Handley, D. A. et al., "Colloidal Gold Labeling Studies Related To Vascular And Endothelial Function, Hemostasis And Receptor–Mediated Processing Of Plasma Macromolecules," European Journal Of Cell Biology, 1987, pp. 163–174, vol. 43.

Hanner, J. et al., "Gianturco Coil Embolization Of Vein Of Galen Aneurysms: Technical Aspects," RadioGraphics, Sep. 1988, pp. 935–946, vol. 8, No. 5.

Heilman, C. B. et al., "Elimination Of A Cirsoid Aneurysm Of The Scalp By Direct Percutaneous Embolization With Thrombogenic Coils," J. Neurosurg., 1990, 298–300, vol. 73.

Heros, R. C., "Intracranial Aneurysms," Minnesota Medicine, Oct. 1990, pp. 27–32, vol. 73.

Hieshima, G. B. et al., "Intracranial Embolotherapy: Plugging Aneurysms With Balloons," Diagnostic Imaging, 1988.

Hilal, S. K. et al., Endovascular Treatment Of Aneurysms With Coils, J. Neurosurg., Feb. 1992, pp. 337–379, vol. 76.

Hilal, S. K. et al., "Synthetic Fiber–Coated Platinum Coils Successfully Used For the Endovascular Treatment Of Arteriovenous Malformations, Aneurysms And Direct Arteriovenous Fistulas Of The CNS," ASNR Twenty–Sixth Annual Meeting, May 15–20, 1988, pp. 224–225.

Hodes, J. E. et al., "Endovascular Occlusino Of Intracranial Vessels For Curative Treatment Of Unclippable Aneurysms: Report of 16 Cases," J. Neurosurg., 1991, pp. 694–701, vol. 75.

Horowitz, M. B. et al., "Scanning Electron Microscopic Findings In A Basilar Tip Aneurysm Embolized With Guglielmi Detachable Coils," AJNR, Apr. 1997, pp. 688–690, vol. 18.

Huckman, M., "Founding Of the Mexican Society Of Diagnostic And Therapeutic Neuroradiology (SMNR)," AJNR, May/Jun. 1992, pp. 1024–1025, vol. 13.

Huckman, M. et al., "Highlights Of the 28$^{th}$ Annual Meeting Of the American Society Of Neuroradiology, Los Angeles, Mar. 19–23, 1990," AJNR, Sep./Oct. 1990, pp. 1055–1063.

Huckman, M. et al., "Meeting Summaries, XIVth Symposium Neuroradiologicum: Jun. 17–23, 1990, the Queen Elizabeth Centre, London," AJNR, Nov./Dec. 1990, pp. 1273–1279, vol. 11.

Ison, K. T., "Platinum And Platinum/Iridium Electrode Properties When Used For Extracochlear Electrical Stimulation Of The Totally Deaf," Medical & Biological Engineering & Computing, Jul. 1987, pp. 403–413, vol. 25.

Kassell, N. F. et al., "The International Cooperative Study On The Timing Of Aneurysm Surgery," J. Neurosurg., 1990, pp. 18–36, vol. 73.

Kassell, N. F. et al., "Timing Of Aneurysm Surgery," Neurosurgery, 1982, pp. 514–519, vol. 10.

Kichikawa, K. et al., "Iliac Artery Stenosis And Occlusion: Preliminary Results Of Treatment With Gianturco Expandable Metallic Stents," Radiology, pp. 799–802, vol. 177, No. 3.

Lammer, J. "Biliary Endoprostheses," Radiologic Clinics Of North America, Nov. 1990, pp. 1211–1222, vol. 28, No. 6.

Lane, B. et al., "Coil Embolization Of An Acutely Ruptuired Saccular Aneurysm," AJNR, Nov./Dec. 1991, pp. 1067–1089, vol. 12.

Leonardi, M., "A History Of Neuroradiology In Italy," AJNR, Apr. 1996, pp. 721–730, vol. 17.

Linton, R., "Intrasaccular Wiring Of Abdominalarteriosclerotic Aortic Aneurysms By The "Pack" Method," Angiology, 1951, pp. 485–498, vol. II.

Linton, R. et al., "Treatment Of Thoracic Aortic Aneurysms By The "Pack" Method Of Intrasaccular Wiring," The New England Journal Of Medicine, Jan.–Jun. 1952, pp. 847–855, vol. 246.

Ljunggren, B. et al., "Early Management Of Aneurysmal Subarachnoid Hemorrhage," Neurosurgery, 1981, pp. 412–418, vol. 11, No. 3.

Loucks, R. B. et al., "The Erosion Of Electrodes By Small Currents," Electrocephalography And Clinical Neurophysiology, 159, pp. 823–826, vol. IX.

Lozier, A. P. et al., "Guglielmi Detachable Coil Embolization Of Posterior Circulation Aneurysms," Stroke, Oct. 2002, pp. 2509–2518.

Lund, G. et al., "Detachable Stainless–Steel Spider," Radiology, Aug. 1983, pp. 167–168, vol. 148, No. 2.

Ljunnggren, B. et al., "Early Operation And Overall Outcome In Aneurysmal Subarachnoid Hemorrhage," J. Neurosurg., Apr. 1985, pp. 547–551, vol. 62.

Manabe, H. et al., "Embolisation Of Ruptured Cerebral Aneurysms With Interlocking Detachable Coils In Acute Stage," Interventional Neuroradiology, 1997, pp. 49–63, vol. 3.

Marshall, M. W. et al., "Ferromagnetism And Magnetic Resonance Artifacts Of Platinum Embolization Microcoils," Cardiovasc. Intervent. Radiol., 1991, pp. 163–166, vol. 14.

Mazer, M. J. et al., "Therapeutic Embolization Of The Renal Artery With Gianturco Coils: Limitations And Technical Pitfalls," Radiology, Jan. 1981, pp. 37–46, vol. 138.

McConnell, A. A., "Subchlasmal Aneurysm Treated By Implantation Of Muscle," Zentralblatt Fur Neurochirurgie, 1937, pp. 269–274, No. 5–6.

McDermott, J. C. et al., "Review Of The Uses Of Digital Roadmap Techniques In Interventional Radiology," CIRSE–SCVIR, Jun. 12–17, 168, pp. 11–13.

McDougall, C.G. et al., "Causes And Management Of Aneurysmal Hemmorage Occurring During Embolization With Guglielmi Detachable Coils," J. Neurosurg., 1998, pp. 87–92, vol. 89.

McDougall, C. G. et al., "Endovascular Treatment Of Basilar Tip Aneurysms Using Electrolytically Detachable Coils," J. Neurosurg., Mar. 1996, pp. 393–399, vol. 84.

McKissock, W., "Anterior Communicating Aneurysms A Trial Of Conservative And Surgical Treatment," The Lancet, Apr. 24, 1965, pp. 873–876.

MDR Database, Brand Name Flex–Tip Guidewire And Tracker Hi–Flow, 1998, Access No. M182232.

Micropaw 20 Micro–Plasma Welding Systems, 1 page.

Miller, D.L., "Arterial Occlusion With Coils," Arch. Intern. Med., Sep. 1985, p. 1737, vol. 145.

Mizoi, K. et al., "A Pitfall In The Surgery Of A Recurrent Aneurysm After Coil Embolization And Its Histological Observation: Technical Case Report," Neurosurgery, Jul. 1996, vol. 39, No. 1.

Molyneux, A. J. et al., "Histological Findings In Giant Aneurysms Treated With Guglielmi Detachable Coils," J. Neurosurg., 1995, pp. 129–132, vol. 83.

Morag et al., "The Role Of Spermatic Venography After Surgical High Ligation Of The Left Spermatic Veins: Diagnosis And Percutaneous Occlusion," Urologic Radiology, 1985, pp. 32–34, vol. 7.

Mullan, S. et al., "Simplified Thrombosis Of A Large, Hypertrophic Hemangioma Of The Scalp," J. Neurosurg., 1964, pp. 68–72, vol. XXI.

Murayama, Y. et al., "Guglielmi Detachable Coil Embolization Of Cerebral Aneurysms: 11 Years' Experience," J. Neurosurg., 2003, pp. 959–966, vol. 98.

Nahser, H. C. et al., "Okklusion Von Aneurysmata Mit Platincolis," Neuroradiologie des Alfred–Krupp–Krankenhauses, pp. 203–207.

Nakahara, I. et al., "Endovascular Coil Embolization Of A Recurrent Giant Internal Carotid Artery Aneurysm Via A Posterior Communicating Artery After Cervical Carotid Litigation: Case Report," Surg. Neurol., 1992, pp. 57–62, vol. 38.

Nakahara, I. et al., "Treatment Of Giant Anterior Communicating Artery Aneurysm Via An Endovascular Approach Using Detachable Balloons And Occlusive Coils," AJNR, Nov./Dec. 1990, pp. 1195–1197, vol. 11.

Nancarrow, P. A. et al., "Stability Of Coil Emboil: An In Vitro Study," Cardiovasc. Intervent. Radiol., 1987, pp. 226–229, vol. 10.

NASA Tech Briefs; "Implantable Electrode For Critical Locations," Aug. 1990, p. 74.

Nishioka H. et al., "Cooperative Study Of Intracranial Aneurysms And Subarachnoid Hemorrhage: A Long–Term Prognostic Study," Arch. Neurol., Nov. 1984, vol. 41.

Numoguchi, Y. et al., "Platinum Coil Treatment Of Complex Aneurysms Of The Vertebrobasilar Circulation," Neuroradiology, 1992, pp. 252–255, vol. 34.

O'Reilly, G. V. et al., "Transcatheter Fiberoptic Laser Coagulation Of Blood Vessels," Radiology, Mar. 1982, pp. 777–779, vol. 142, No. 3.

Okazaki, M. et al., "A Coaxial Catheter And Steerable Guidewire Used To Embolize Branches Of The Splanchnic Arteries," AJR, Aug. 1990, pp. 405–406, vol. 155.

Padolecchia, R. et al., "Role Of Electrothrombosis In Aneurysm Treatment With Guglielmi Detachable Coils: An In Vitro Scanning Electron Microscopic Study," AJNR, Oct. 2001, pp. 1757–1760, vol. 22.

Pakarinen, S., "Incidence, Aetiology And Prognosis Of Primary Surarachnoid Haemorrhage," Acta Neurologica Scandinavica, 1967, pp. 9–128, Supplementum 29, vol. 43.

Parsonnet, V. et al., "Corrosion Of Pacemaker Electrodes," Pace, May–Jun. 1981, pp. 289–297, vol. 4.

Peerless, S. J. et al., "Giant Intracranial Aneurysms," Vascular Disease, Chapter 57, 1987, pp. 1742–1763.

Peterson, E. W. et al., (abstract) "291. Electrically Induced Thrombosis Of The Cavernous Sinus In The Treatment Of Carotid Cavernous Fistula," Fourth International Congress Of Neurological Surgery Ninth International Congress Of Neurology, Sep. 20–27, 1969, p. 105.

Probst, P. et al., "Nonsurgical Treatment Of Splenic–Artery Aneurysms," Radiology, Jul.–Sep. 1978, pp. 619–623, vol. 128.

Probst, P. et al., "Which Embolic Material Is Best Suited For Which Embolization Procedure?" Fortschr. Rontgenstr., 1978, pp. 447–454, vol. 129, No. 4.

Quinn, S. F. et al., "Complications From 0.018–in. Floppy Platinum–Tip Guidewires," AJR, May 1990, pp. 1103–1104, vol. 154.

Ralston, M. D. et al., "Effect Of Increasing Current And Decreasing Blood Flow For Transcatheter Electrocoagulation (TCEC)," Investigative Radiology, Mar.–Apr. 1982, pp. 171–177, vol. 17, No. 2.

Rao, V. R. et al., "Embolization Of Large Saccular Aneurysms With Gianturco Coils," Radiology, 1990, pp. 407–410, vol. 175.

"Reaction To The Inventive Step Arguments From The Groeneveld Report Of Nov. 4, 2002 on EP–B–0 484 468, EP–B–0 800 790, EP–B–0 804 905 in the case EV3 et al./The Regents & Boston," 11 pages.

"Replication Of The Thompson et al. Transcatheter Electrocoagulation Experimental Evaluation Of The Anode Experiments," Apr. 30, 2003, 16 pages.

Reul, J. et al., "Long–Term Angiographic And Histopathologic Findings In Experimental Aneurysms Of The Carotid Bifurcation Embolized With Platinum And Tungsten Coils," AJRN, Jan. 1997, pp. 35–42, vol. 18.

Rodriguez, F., "Principles Of Polymer Systems," Second Edition, 1982, pp. 534–537.

Rufenacht, D. et al., "Principles And Methodology Of Intracranial Endovascular Access," Interventional Neuroradiology, May 1992, pp. 251–268, vol. 2, No. 2.

Ruscalleda, J. et al., "Neuroradiological Features Of Intracranial And Intraorbital Meningeal Haemangiopericytomas," Neuroradiology, 1994, pp. 440–445, vol. 36.

Russell, E., "Highlights Of The Scientific Exhibits Of The $29^{th}$ Annual Meeting Of The American Society Of Neuroradiology, Washington, D.C., Jun. 9–14, 1991," pp. 1251–1257.

Sadato, A. et al., "Immediately Detachable Coil For Aneurysm Treatment," AJRN, Aug. 1995, pp. 1459–1462, vol. 16.

Salazar, A. E., "Experimental Myocardial Infarction," Circulation Research, Nov. 1961, vol. IX.

Samuelsson, L. et al., "Electrocoagulation," Acta Radiologica Diagnosis, 1982, pp. 459–462, vol. 23.

Samuelsson L. et al., "Electrolytic Destruction Of Tissue In The Normal Lung Of the Pig," Acta Radiologica Diagnosis, 1981, pp. 9–14, vol. 22.

Sawyer, P. N. et al., "Electrical Potential Differences Across The Normal Aorta And Aortic Grafts Of Dogs," Am. J. Physiol., Oct. 1953, pp. 113–117, vol. 175.

Serbinenko, F. A., "Balloon Catheterization And Occlusion Of Major Cerebral Vessels," J. Neurosurg., Aug. 1974, vol. 41.

Setton, A. et al., "Interventional Neuroradiology," Current Opinion In Neurology And Neurosurgery, 1992, pp. 870–880, vol. 5.

Shah, P. M. et al., "Pseudoaneurysm Of Anterior Tibial Artery After Occlusion From Blunt Trauma: Nonoperative Management," The Journal of Trauma, 1985, pp. 656–657, vol. 25, No. 7.

Shimizu, S. et al., "Tissue Response Of A Small Saccular Aneurysm After Incomplete Occlusion With A Guglielmi Detachable Coil," AJNR, Apr. 1999, pp. 546–548, vol. 20.

Sorteberg, A. et al., "Effect Of Guglielmi Detachable Coils On Intraaneurysmal Flow: Experimental Study In Canines," AJNR, Feb. 2002, pp. 288–294, vol. 23.

Sosman, M. C. et al., "Aneurysms Of The Internal Carotid Artery And The Circle Of Willis, From A Roentgenological Viewpoint," The American Journal Of Roentgenology And Radium Therapy, Jan.–Jun. 1926, vol. XV.

Steiner, L., "Gamma Knife Radiosurgery In Arteriovenous Malformations Of The Brain," 6 pages.

Strother, C., "Electrothrombosis Of Saccular Aneurysms Via Endovascular Approach Part 1 and Part 2," AJNR, May 2001, pp. 1010–1012, vol. 22.

Taki, W. et al., "Balloon Embolization Of A Giant Aneurysm Using A Newly Developed Catheter," Surg. Neurol., Nov. 1979, pp. 363–365; vol. 12.

Taki, W. et al., "Radiopaque Solidifying Liquids For Releasable Balloon Technique: A Technical Note," Surg. Neurol., Feb. 1980, pp. 140–142, vol. 13.

Terbrugge, K., "Duram AVMs Of The Posterior Fossa: Clinical Presentation, Classification, Angiographic Evaluation And Treatment," 4 pages.

"Third Amendment After Final In U.S. Appl. No. 10/170,897," Dec. 2, 2002, 4 pages.

Thompson, W. M. et al., "Vessel Occlusion With Transcatheter Electrocoagulation," Cardiovasc. Intervent. Radiol., 1980, pp. 244–255, vol. 3, No. 4.

Thompson, W. M. et al., "Vessel Occlusion With Transcatheter Electrocoagulation: Initial Clinical Experience," Radiology, Oct.–Dec. 1979, pp. 335–340, vol. 133.

Tragardh, Bengi et al., "Intravascular Electrically Induced In The Dog," Radiology, Oct.–Dec. 1976, pp. 55–56, vol. 121.

Vinuela, F. et al., "Electrolytically Detachable Microcoils," AJNR, Mar./Apr. 1993, pp. 337–339, vol. 14.

Vinuela, F. et al., "Embolization Of Brain AVMs With Liquids," 4 pages.

Wallace, S. et al., "Steel Coil Embolus And Its Therapeutic Applications," Abrams Angiography, 1983, pp. 2151–2173, Third Edition, vol. III.

Werner, S. C. et al., "Aneurysm Of The Internal Carotid Artery Within The Skull," The Journal Of The American Medical Association, Jan.–Jun. 1941, pp. 578–582, vol. 116.

Wiebers, D. O. et al., "Impact Of Unruptured Intracranial Aneurysms On Public Health In The United States," Stroke, Oct. 1992, pp. 1416–1419, vol. 23, No. 10.

Wiebers, D. O. et al., "The Significance Of Unruptured Intracranial Saccular Aneurysms," J. Neurosurg., Jan. 1987, pp. 23–29, vol. 66.

White Jr., R. I. et al., "Therapeutic Embolization With Long–Term Occluding Agents And Their Effects On Embolized Tissues," Radiology, Dec. 1977, pp. 677–687, vol. 125.

Workman, M. et al., "Thrombus Formation At The Neck Of Cerebral Aneurysms During Treatment With Guglielmi Detachable Coils," AJNR, Oct. 2002, pp. 1568–1576, vol. 23.

Yoneda, S. et al., "Electrothrombosis Of Aterovenous Malformation," Neurologia Medico–Chirurgica, 1997, pp. 19–28, vol. 17, Part I, No. 1.

Yoneda, S. et al., "Treatment Of Spontaneous Carotid–Cavernous Fistula," Neurol. Med. Chir., 1979, pp. 141–147, vol. 10.

Yoshida, K., "Experimental Studies On The Production And Treatment Of The Carotid Thrombosis In Dogs," Archiv fur Japanische Chirurgie, May 1964, pp. 502–524, vol. 33, No. 3.

Yuen, T. G. H. et al., "Tissue Response To Potential Neuroprosthetic Materials Implanted Subdurally," Biomaterials, Mar. 1987, pp. 138–140, vol. 8.

Zollikofer, C. et al., "A Combination Of Stainless Steel Coil And Compressed Ivalon: A New Technique For Embolization Of Large Arteries And Arteriovenous Fistulas," Radiology, Jan.–Mar. 1981, pp. 229–231, vol. 138.

Alksne et al. "Stereotaxic Occlusion of 22 Consecutive Anterior Communicating Artery Aneurysms," J. Neurosurg., 1980, pp. 790–793, vol. 52.

Anderson et al., "Transcatheter Intravascular Coil Occlusion Of Experimental Arteriovenous Fistulas," Am. J. Roentgenology, Oct./Nov. 1977, pp. 795–798, vol. 129.

Araki et al., "Electrically Induced Thrombosis For The Treatment Of Intracranial Aneurysms And Angiomas," Department of Neurosurgery, Kyoto University Medical School, Kyoto, Japan, pp. 651–654.

ASNR Section, Highlights of the 28$^{th}$ Annual Meeting of the American Society of Neuroradiology, Los Angeles, CA, Mar. 19–23, pp. 1057–1069, 1990.

Braun et al. "Use Of Coils For Transcatheter Carotid Occlusion," AJNR, Dec. 1985, pp. 953–956, vol. 6.

Castaneda–Zuniga et al., "A New Device For The Safe Delivery Of Stainless Steel Coils," Radiology, Jul. 1980, pp. 230–131, vol. 136.

Claiborne Johnston et al. "Recommendation For The Endovascular Treatment Of Intracranial Aneurysms," Stroke, 2002, pp. 2536–2544, vol. 33.

Cook Catalog with Hilal–Coils, 1988, pp. 1–5.

Cragg et al. "Nonsurgical Placement of Arterial Endoprostheses: A New Technique Using Nitinol Wire", Radiology, Apr. 1983, pp. 261–263, vol. 147.

Debrun et al. "Detachable Balloon and Calibrated–leak balloon techniques in the treatment of cerebral vascular lesions," J. Neurosurg, 1978, pp. 635–649, vol. 49.

Donauer et al., "Intracranial Aneurysms: The surgical and Endovascular Approach," Dendron, 2002, Lanzer and Topol eds., Springer Verlag, pp. 1154–1216.

Dovey et al. "Guglielmi Detachable Coiling For Intracranial Aneurysms," Arch Neurol., 2001, pp. 559–564, vol. 58.

Dowd et al. "Endovascular Coil Embolization Of Unusual Posterior Inferior Cerebellar Artery Aneurysms," Neurosurgery, 1990, pp. 954–961, vol. 27.

Gianturco et al., "Mechanical Devices For Arterial Occlusion", Am. J. Roentgenology Radium Therapy and Nuclear Medicine (AJR), 1975, pp. 428–435, vol. 124.

Graves et al., "Treatment Of Carotid Artery Aneurysms With Platinum Coils: An Experimental Study In Dogs," AJNR, 1990, pp. 249–252, vol. 11.

Guerrisi et al. "L'elettrotrombosi Intravasale Nelle Malformazioni Vascolari Sperimentalmente Provocate," Proceedings of the Bari Congress, Sep. 29/30, 1983, pp. 159–146, translation included.

Guglielmi, G., "Historical Note," AJNR, 2002, p. 342, vol. 23.

Guglielmi, G., "Embolization Of Intracranial Aneurysms With Detachable Coils And Electrothrombosis," Interventional Neuradiology: Endovascular Therapy of the Central Nervous System, Ed. F. Vinuela et al. Raven Press, New York, 1992, pp. 63–75.

Guglielmi et al., "Electrothrombosis Of Saccular Aneurysms Via Endovascular Approach, Part 1: Electrochemical Basis, Technique, And Experimental Results," J. Neurosurg., 1991, pp. 1–7, vol. 75.

Guglielmi et al., "Electrothrombosis Of Saccular Aneurysms Via Endovascular Approach, Part 21: Preliminary Clinical Experience," J. Neurosurg., 1991, pp. 8–14, vol. 75.

Hanner et al., "Gianturco Coil Embolization Of Vein Of Galen Aneurysms: Technical Aspects," Radiographics, Sep. 1988, pp. 935–946, vol. 8, No. 5.

Hawkins et al., "Retrievable Gianturco–Coil Introducer," Radiology, Jan. 1986, pp. 262–264.

Higashida et al., "Interventional Neurovascular Treatment Of A Giant Intracranial Aneurysm Using Platinum Microcoils," Surg. Neurol., Jan. 1991, pp. 64–68, vol. 35, No. 1.

Hilal et al., "Synthetic Fiber–Coated Platinum Coils Successfully Used for the Endovascular Treatment of Arteriovenous Malformations, Aneurysms And Direct Arteriovenous Fistulas Of The CNS," 26$^{th}$ Annual Meeting, Session 10G, Paper 175, 1988.

Hilal Coils In Cook Incorporated Catalog, 1988, 9 pages.

Hosobuchi, Y., "Electrothrombosis Of Carotid–Cavernous Fistula," J. Neurosurg., Jan. 1975, pp. 76–85, vol. 42.

Hunner, G.L., "Aneurysm Of The Aorta Treated By The Insertion Of A Permanent Wire And Galvanism Moore–Corradi Method," Bulletin of the Johns Hopkins Hospital; 1900, pp. 263–279, vol. XI, No. 116.

Konishi et al., "Congenital Fistula Of The Dural Carotid–Cavernous Sinus: Case Report And Review Of The Literature," Neurosurgery, 1990, pp. 120–125, vol. 27, No. 1.

Lund et al., "Detachable Steel Spring Coils For Vessel Occlusion," Radiology, May 1985, p. 530, vol. 155.

Marsman et al., "A Safe Technique For The Delivery Of 'Mini' Gianturco Stainless Steel Coils," Diagnostic Imaging, 1981, pp. 43–46, vol. 50.

McAlister et al., "Occlusion Of Acquired Renal Arteriovenous Fistula With Transcatheter Electrocoagulation," Am. J. Roentgenol., Jun. 1979, pp. 998–1000, vol. 132.

McAlister et al., "Transcatheter Electrocoagulation Of The Pulmonary Artery: An Experimental Model In Dogs For Studying Pulmonary Thrombosis," Invest Radiol., 1981, pp. 289–297, vol. 16.

MDR Database, Brand Name Target Therapeutics, 1990, Access No. M183708.

MDR Database, Brand Name Target Therapeutics Tracker 18 LF Catheter, 1990, Access No. M220254.

MDR Database, Brand Name Target Therapeutics Tracker 18 Catheter, 1991, Access No. M235647.

MDR Database, Brand Name Tracker 18 Dual Marker, Jan. 1992, Access No. M264109.

MDR Database, Brand Name Target Therapeutics Coil Pusher 16, Jan. 1990, Access No. M183709.

MDR Database, Brand Name Target Therapeutics Coil Pusher 16, Dec. 1989, Access No. M181514.

MDR Database, Brand Name 10 Unibody Infusion Catheter, May 1991, Access No. M231556.

MDR Database, Brand Name Target Therapeutics Tracker 18 Unibody Catheter, Oct. 1991, Access No. M246650.

Miller et al., "Clinical Use Of Transcatheter Electrocoagulation," Radiol., 1978, pp. 211–214, vol. 129.

Morse et al., "Platinum Microcoils For Therapeutic Embolization: Nonneuroradiologic Applications," AJR, 1990, pp. 401–403, vol. 155.

Mullan et al., "Electrically Inducted Thrombosis In Intracranial Aneurysms," J. Neurosurg., Jan.–Jun. 1985, pp. 539–547, vol. 22.

Mullan, S., "Experiences with Surgical Thrombosis of Intracranial Berry Aneurysms and Cartotid Cavernour Fistulas," J. Neurosurg., 1974, pp. 657–670, vol. 41.

Mullan et al., "Stereotactic Copper electric Thrombosis of Intracranial Aneurysms," Progr. Neurol. Surg., 1969, pp. 193–211, vol. 2.

Ovitt et al., "Guide Wire Thrombogenicity And Its Reduction," Radiology, 1974, pp. 43–46, vol. 111, No. 1.

Phillips, J., "Transcatheter Electrocoagulation Of Blood Vessels," Invest. Rad., 1973, pp. 295–304, vol. 8.

Philpott et al., "The Mechanism Of Transcatheter Electrocoagulation (TCEC)," Investigative Radiology, 1983, pp. 100–104, vol. 18.

Piton et al., "Selective Vascular Thrombosis Induced By A Direct Electrical Current: animal experiments," J. Neuroradiology, 1978, pp. 139–152, vol. 5.

Piton et al., "Vascular Thrombosis Induced By Direct Electrical Current," Neuroradiology, 1978, pp. 385–388, vol. 16.

Piton et al., "Embolisation Par Courant Electrique Continu : ECEC," J. Radiol., 1979, pp. 799–808, vol. 60. No. 12 (including English translation).

Sawyer et al., "Bio–Electric Phenomena as an Etiological Factor in Intravascular Thrombosis," Am. J. Physiol., 1953, pp. 103–107, vol. 175.

Serbinenko, F., "Balloon Catherization And Occlusion Of Major Cerebral Vessels," J. Neurosurg., 1974, pp. 125–145, vol. 41.

Strother, C., ed., "Electrothrombosis Of Saccular Aneurysms Via Endovascular Approach: Part 1 and Part 2", AJNR, 2002, pp. 1011–1012, vol. 22.

Taki et al., "Selection And Combination Of Various Endovascular Techniques In The Treatment Of Giant Aneurysms," J. Neurosurg., 1992, pp. 37–42, vol. 77.

Taki et al., "Radiopaque Solidifying Liquids For Releasable Balloon Technique: A Technique Note," Surg. Neurol., 1980, pp. 140–142, vol. 13.

Target Therapeutics Catalogue 1993–95, 1997, 2003.

Target Therapeutics, "History of the Guglielmi Detachable Coil," History of the GDC, Oct. 1995, pp. 1–6.

Thompson et al., "Transcatheter Electrocoagulation: A Therapeutic Angiographic Technique For Vessel Occlusion," Invest. Radiol., 1977, pp. 146–153, vol. 12.

Thompson et al., "Transcatheter Electrocoagulation: Experimental Evaluation Of The Anode," Invest. Radiol., 1979, pp. 41–47, vol. 14.

Thompson et al., "Vessel Occlusion With Transcatheter Electrocoagulation," Cardio Vasc. Intervent. Radiol., 1980, pp. 244–245, vol. 3.

Thompson et al., "Vessel Occlusion With Transcatheter Electrocoagulation: Initial Clinical Experience," Radiol., 1979, pp. 335–340, vol. 133.

Wallace et al., "Therapeutic Vascular Occlusion Utilizing Steel Coil Technique: Clinical Applications," American J. Roentgenology, 1976, pp. 381–387, vol. 127.

Yang et al., "Platinum Wire: A New Transvascular Embolic Agent," AJNR, May/Jun. 1988, pp. 547–550, vol. 9.

Byrne, J.V. et al., "The Nature Of Thrombosis Induced By Platinum And Tungsten Coils In Saccular Aneurysms," Am J. Neuroradiology, Jan. 1997, pp. 29–33, vol. 18.

"Excelsior 1018 Microcatheter," Boston Scientific Therapeutic, 2000, 4 pages.

"Guglielmi Detachable Coil (GDC®) Product Information Summary," 36 pages.

Guglielmi, G. et al., "Detachable Microcoils In The Endovascular Treatment Of Intracranial Aneurysms: Preliminary Clinical Experience," Endovascular Therapy, Session VII/Paper 35, p. 73.

Guglielmi, G. et al., "Endovascular Treatment Of Posterior Circulation Aneurysms By Electrothrombosis Using Electrically Detachable Coils," J. Neurosurg., Oct. 1992, pp. 515–524.

Horowitz, M. et al., "Does Electrothrombosis Occur Immediately After Embolization Of An Aneurysm With Guglielmi Detachable Coils," AJNR, Mar. 1997, pp. 510–513, vol. 18.

Johnston, S.C. et al., "Recommendations For The Endovascular Treatment Of Intracranial Aneurysms," Stroke, 2002, pp. 2536–2544, vol. 33.

Konishi Y. et al., "Evaluation Of Acute Thrombogenesis Of Microcoil For Treatment Of Experimental Aneurysms," 1 page.

Linton, R. R. et al., "Treatment Of Thoracic Aortic Aneurysms By The "Pack" Method Of Intrasaccular Wiring," The New England Journal Of Medicine, Jan.–Jun. 1952, pp. 847–855, vol. 246.

Lylyk, P. et al., "Therapeutic Alternatives For Vein Of Galen Vascular Malformations," J. Nurosurg., Mar. 1993, pp. 438–445, vol. 78.

Malisch, T. et al., "What You Should Know About Aneurysms," brochure, 6 pages.

Marsman, J.W.P. et al., "A Safe Technique For The Delivery Of 'Mini' Gianturco Stainless Steel Coils," Diagnostic Imaging, 1981, pp. 43–46, vol. 50.

McAlister, D.S. et al., "Occlusion Of Acquired Renal Arteriovenous Fistula With Transcatheter Electrocoagulation," AJR, Jun. 1979, pp. 998–1000, vol. 132.

Mehringer, C.M. et al., "Therapeutic Embolization For Vascular Trauma Of The Head And Neck," AJNR, pp. 137–142, Mar.–Apr. 1983, vol. 4.

Murayama, Y. et al., "Ion Implantation: A New Experimental Approach To Surface Modification Of Electrolytically Detachable Coils," 1 page.

Pevsner, Paul, "Micro–Balloon Catheter for Superselective Angiography and Therapeutic Occlusion," AMJR, Feb. 1977, pp. 225–230, vol. 128.

Phillips, J.F. et al., "Experimental Closure Of Arteriovenous Fistula By Transcatheter Electrocoagulation," Diagnostic Radiology, May 1975, pp. 319–321, vol. 115.

Phillips, J.F., "Transcatheter Electrocoagulation Of Blood Vessels," Investigative Radiology, Sep.–Oct. 1973, pp. 295–304, vol. 8.

"Prowler Select: Microcatheter Select Performance," Cordis, 3 pages.

Quereshi, A.I. et al., "Endovascular Treatment Of Intracranial Aneurysms By Using Guglielmi Detachable Coils In Awake Patients: Safety And Feasability," Neurosurgery Focus, May 2001, pp. 1–6, vol. 10, No. 5.

"Renegade Fiber Braided Microcatheter," Boston Scientific Target, 1998, 4 pages.

Sadato, A. et al., "Treatment Of A Spontaneous Carotid Cavernous Fistula Using An Electrodetachable Microcoil," AJNR, Mar./Apr. 1993, pp. 334–336, vol. 14.

"Seeker Flexible 16," Target Therapeutics, 1 page.

"Seeker Lite™—10 Steerable Guidewire," Target Therapeutics, 1 page.

"Seeker® Standard 14 Steerable Guidewire," Target Therapeutics, 1 page.

"Spinnaker™ 1.8F–L w/Hydrolene® Flow Directed Catheter," Target Therapeutics, 1 page.

Strother, C.M., "Electrothrombosis Of Saccular Aneurysms Via Endovascular Approach: Part 1 And Part 2," Historical Perspective, AJNR, May 2001, pp. 1011–1012, vol. 22.

"Target Therapeutics: Recommended Start Up Products: Guglielmi Detachable Coil (GDC) (Investigational Device)," 1 page.

"Tracker®—18 Hi–Flow Infusion Catheter Applications," Target Therapeutics, 1 page.

"Tracker®—18 Hi–Flow Infusion Catheter Specifications," Target Therapeutics, 1 page.

"Tracker® Excel™—14 Microcatheter Engineered For GDC® Coil Delivery," Boston Scientific Target, 1998, 4 pages.

Berenstein, A., et al., "Transvascular Treatment of Giant Aneurysms of the Cavernous Carotid and Vertebral Arteries," Surg Neurol, 1984, pp. 3–12, vol. 21.

Canadian Patent Application No. 2,160,640 Patent Application Status, 1 page.

Canadian Patent Application No. 2,055,492, Patent Application File History, 93 pages.

Canadian Patent Application No. 2,179,863 Patent Application File History, 39 pages.

Castaneda–Zuniga, W. et al., "A New Device for the Safe Delivery of Stainless Steel Coils," Radiology, Jul. 1980, pp. 230–231, vol. 136.

Debrun, G. et al., "Experimental Approach to the Treatment of Carotid Cavernous Fistulas with an Inflatable and Isolated Balloon," Neuroradiology, 1975, pp. 9–12, vol. 9.

Fox, A.J. et al., "Use of Detachable Balloons for Proximal Artery Occlusion in the Treatment of Unclippable Cerebral Aneurysms," J Neurosurg, 1987, pp. 40–46, vol. 66.

Halbach, V.V. et al., "Transvenous Embolization of Direct Carotid Cavernous Fistulas," AJNR, Jul./Aug. 1988, pp. 741–747, vol. 9.

Kwan, E.S.K. et al., "Enlargement of Basilar Artery Aneurysms Following Balloon Occlusion—"Water Hammer Effect"" J Neurosurg, 1991, pp. 963–968, vol. 75.

Massoud, T.F. et al., "Laboratory Simulations and Training in Endovascular Embolotherapy with a Swine Arteriovenous Malformation Model," AJNR, Feb. 1996, pp. 271–279, vol. 17.

Mickle, J.P. et al., "The Transtorcular Embolization of Vein of Galen Aneurysms," J. Neurosurg., May 1986, vol. 64, pp. 731–735.

Purdy, P.D., "Imaging Cerebral Blood Flow in Interventional Neuroradiology: Choice of Technique and Indications," AJNR, May/Jun. 1991, pp. 424–427, vol. 12.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–23 is confirmed.

* * * * *